US008637684B2

(12) United States Patent
Shen et al.

(10) Patent No.: US 8,637,684 B2
(45) Date of Patent: Jan. 28, 2014

(54) TAUTOMYCETIN AND TAUTOMYCETIN ANALOG BIOSYNTHESIS

(75) Inventors: Ben Shen, Verona, WI (US); Zhong-Yin Zhang, Indianapolis, IN (US)

(73) Assignees: Wisconsin Alumni Research Foundation, Madison, WI (US); Indiana University Research and Technology Corporation, Indianapolis, IN (US)

(*) Notice: Subject to any disclaimer, the term of this patent is extended or adjusted under 35 U.S.C. 154(b) by 0 days.

(21) Appl. No.: 13/101,612

(22) Filed: May 5, 2011

(65) Prior Publication Data

US 2011/0281942 A1 Nov. 17, 2011

Related U.S. Application Data

(60) Provisional application No. 61/333,993, filed on May 12, 2010, provisional application No. 61/361,814, filed on Jul. 6, 2010.

(51) Int. Cl.
*C07D 303/00* (2006.01)
*C12P 17/04* (2006.01)

(52) U.S. Cl.
USPC .......................................... 549/323; 435/126

(58) Field of Classification Search
USPC .......................................... 549/323; 435/126
See application file for complete search history.

(56) References Cited

U.S. PATENT DOCUMENTS

2012/0010282 A1  1/2012  Shen

OTHER PUBLICATIONS

Alder, et al., "Tautomycetin and tautomycin suppress the growth of medullary thyroid cancer cells via inhibition of glycogen synthase kinase-3beta," *Mol. Cancer Ther.*, 8:914-20, 2009.
Cheng, et al., "A new antibiotic, tautomycin," *J. Antibiot.*, 40:907-9, 1987.
Cheng, et al., "The structure of tautomycetin, a dialkylmaleic anhydride antibiotic," *J. Antibiot.*, 43:890-6, 1990.
Cheng, et al., "The structure of tautomycin, a dialkylmaleic anhydride antibiotic," *J. Antibiot.*, 43:809-19, 1990.
Choi, et al., "Isolation of the biosynthetic gene cluster for tautomycetin, a linear polyketide T cell-specific immunomodulator from *Streptomyces* sp. CK4412," *Microbiology*, 153:1095-102, 2007.
Colby, et al., "A new model of the tautomycin-PP1 complex that is not analogous to the corresponding okadaic acid structure," *Bioorg. Med. Chem. Lett.*, 13:1601-5, 2003.
Han, et al., "Tautomycetin as a novel immunosuppressant in transplantation," *Transplant. Proc.*, 35:547, 2003.
Hur, et al., "Identification of TmcN as a pathway-specific positive regulator of tautomycetin biosynthesis in *Streptomyces* sp. CK4412," *Microbiology*, 154:2912-9, 2008.

Ju, et al., "Functional characterization of ttmM unveils new tautomycin analogs and insight into tautomycin biosynthesis and activity," *Org. Lett.*, 11:1639-42, 2009.
Kelker, et al., "Crystal structures of protein phosphatase-1 bound to nodularin-R and tautomycin: a novel scaffold for structure-based drug design of serine/threonine phosphatase inhibitors," *J. Mol. Biol.*, 385:11-21, 2009.
Lee, et al., "Tautomycetin inhibits growth of colorectal cancer cells through p21cip/WAF1 induction via the extracellular signal-regulated kinase pathway," *Mol. Cancer Ther.*, 5:3222-31, 2006.
Li, et al., "Characterization of the tautomycetin biosynthetic gene cluster from *Streptomyces griseochromogenes* provides new insight into dialkylmaleic anhydride biosynthesis," *J. Nat. Prod.*, 72:450-9, 2009.
Li, et al., "Characterization of the tautomycin biosynthetic gene cluster from *Streptomyces spiroverticillatus* unveiling new insights into dialkylmaleic anhydride and polyketide biosynthesis," *J. Biol. Chem.*, 283:28607-17, 2008.
Liu, et al., "SHP2 is a target of the immunosuppressant tautomycetin," *Chem. Biol.*, 18:101-10, 2011.
Luo, et al., "Functional characterization of TtnD and TtnF, unveiling new insights into tautomycetin biosynthesis," *J. Am. Chem. Soc.*, 132:6663-71, 2010.
Luo, et al., "Protein phosphatase 1 regulates assembly and function of the beta-catenin degradation complex," *EMBO J.*, 26:1511-21, 2007.
MacKintosh, et al., "Cyanobacterial microcystin-LR is a potent and specific inhibitor of protein phosphatases 1 and 2A from both mammals and higher plants," *FEBS Lett.*, 264:197-92, 1990.
Mitsuhashi, et al., "Tautomycetin is a novel and specific inhibitor of serine/threonine protein phosphatase type 1, PP1," *Biochem. Biophys. Res. Commun.*, 21:328-31, 2001.
Mitsuhashi, et al., "Tautomycetin suppresses the TNFalpha/NF-kappaB pathway via inhibition of IKK activation," *Int. J. Oncol.*, 33:1027-35, 2008.
Mitsuhashi, et aL., "Usage of tautomycetin, a novel inhibitor of protein phosphatase 1 (PP1), reveals that PP1 is a positive regulator of Raf-1 in vivo," *J. Biol. Chem.*, 278:82-8, 2003.
Nishiyama, et al., "Structure-activity relationship within a series of degradation products of tautomycin," *Biosci. Biotechnol. Biochem.*, 60:103-7, 1996.
Oikawa, et al., "Synthesis of specific protein phosphatase inhibitors, tautomycin and tautomycetin toward structure-activity relationship study," *Curr. Med. Chem.*, 9:2033-53, 2002.
Sheppeck, et al., "Total Synthesis of the Serine/Threonine-Specific Protein Phosphatase Inhibitor Tautomycin(1)," *J. Org. Chem.*, 62:387-98, 1997.
Shim, et al., "Immunosuppressive effects of tautomycetin in vivo and in vitro via T cell-specific apoptosis induction," *Proc. Natl. Acad. Sci. USA*, 99:10617-22, 2002.
Sugiyama, et al., "Molecular shape analysis and activity of tautomycin, a protein phosphatase inhibitor," *Bioorg. Med. Chem. Lett.*, 6:3-8, 1996.
Takai, et aL., "Effects of modification of the hydrophobic C-1-C-16 segment of tautomycin on its affinity to type-1 and type-2A protein phosphatases," *Biochem. J.*, 350:81-8, 2000.

(Continued)

*Primary Examiner* — Nizal Chandrakumar
(74) *Attorney, Agent, or Firm* — Parker Highlander PLLC

(57) ABSTRACT

The present invention relates to tautomycetin (TTN) and analogs thereof. Also provided are methods of using TTN and analogs thereof in the treatment of various diseases relating to SHP2 function.

38 Claims, 12 Drawing Sheets

(56) References Cited

OTHER PUBLICATIONS

Takai, et al., "Inhibition of specific binding of okadaic acid to protein phosphatase 2A by microcystin-LR, calyculin-A and tautomycin: method of analysis of interactions of tight-binding ligands with target protein," *Biochem. J.*, 306:657-65, 1995.

Zhang and Zhang, "PTP1B as a drug target: recent developments in PTP1B inhibitor discovery," *Drug Discov. Today*, 12:373-81, 2007.

Zhang, et al., "Salicylic acid based small molecule inhibitor for the oncogenic Src homology-2 domain containing protein tyrosine phosphatase-2 (SHP2).," *J. Med. Chem.*, 53:2482-93, 2010.

Oikawa et al. Tetrahedron Letters, vol. 38, Issue 45, Nov. 10, 1997, pp. 7897-7900.

Office Action issued in co-pending U.S. Appl. No. 13/101,624, dated Nov. 2, 2012.

TAUTOMYCETIN AND TAUTOMYCETIN ANALOG BIOSYNTHESIS

This application claims benefit of priority to U.S. Provisional Application Ser. No. 61/333,993, entitled "Materials and Methods For Inhibiting SHP2 Tautomycetin And Derivatives Thereof," filed May 12, 2010, and U.S. Provisional Application Ser. No. 61/361,814, filed Jul. 6, 2010, the entire contents of both applications being hereby incorporated by reference.

This invention was made with government support under CA113297 awarded by the National Institutes of Health. The government has certain rights in the invention.

BACKGROUND OF THE INVENTION

I. Technical Field

The present invention relates generally to the fields of microbiology and bacterial genetics. More particularly, it tautomycetin (TTN) analogs and uses therefor.

II. Related Art

The Src homology-2 domain containing protein tyrosine phosphatase-2 (SHP2) is a positive transducer of growth factor- and cytokine-mediated signaling pathways essential for cell proliferation, differentiation, migration, and apoptosis (Neel et al., 2003). The catalytic activity of SHP2 is required for full activation of the Ras-ERK1/2 cascade that is mediated through SHP2-catalyzed dephosphorylation of substrates that are negatively regulated by tyrosine phosphorylation (Neel et al., 2003; Tiganis and Bennett, 2007). Not surprisingly, SHP2 has been identified as a bona fide oncogene from the protein tyrosine phosphatase (PTP) superfamily; gain-of-function SHP2 mutations leading to increased PTP activity are known to cause the autosomal dominant disorder Noonan syndrome as well as multiple forms of leukemia and solid tumors (Tartaglia and Gelb, 2005; Chan et al., 2008). Accordingly, SHP2 represents an exciting target for multiple cancers.

Unfortunately, obtaining SHP2 inhibitors with optimal potency and pharmacological properties has been difficult, due primarily to the highly conserved and positively charged nature of the active site pocket shared by all PTP family members.

Tautomycin (TTM) and tautomycetin (TTN) are polyketide natural products originally isolated as antifungal antibiotics from *Streptomyces spiroverticillatus* and *Streptomyces griseochromogens*, respectively (Cheng et al., 1987; Cheng et al., 1989) (FIGS. 1A-B). They are structurally similar, differing only in the presence of a spiroketal group on TTM, which is replaced by a dienone moiety in TTN. TTM and TTN were later found to display inhibitory activity against serine/threonine protein phosphatase 1 (PP1) and 2A (PP2A) (MacKintosh and Klumpp, 1990; Mitsuhashi et al., 2001). Despite their similarities in structure and PP1/2A inhibitory activity, TTN, but not TTM, has been identified as a potent immunosuppressor of activated T cells in organ transplantation (Shim et al., 2002; Han et al., 2003). TTN exerts its immunosuppressive activity by blocking T-cell receptor (TCR) induced tyrosine phosphorylation, leading to inhibition of T cell proliferation and cell-specific apoptosis (Shim et al., 2002). Furthermore, TTN has also been suggested as a potential lead for anticancer drug discovery due to its growth inhibitory activity against colorectal cancer cells (Lee et al., 2006). Thus, TTN may serve as a promising lead for the development of new immunosuppressive and anti-tumor agents. To this end, identification of the cellular target(s) of TTN will significantly advance the progress toward TTN-based therapeutics. Strikingly, although TTM and TTN exhibit similar potency toward PP1/PP2A, TTM, unlike TTN, has no effect on tyrosine phosphorylation in T cells and does not elicit any immunosuppressive activity (Shim et al., 2002). Consequently, the immunosuppressive activity of TTN is unlikely related to its PP1/PP2A inhibitory activity and instead may be mediated by an effect on a PTP.

SUMMARY OF THE INVENTION

Thus, in accordance with the present invention, there is provided a compound having the formula:

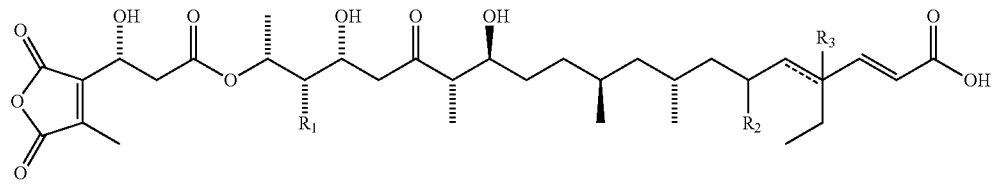

wherein $R_1$ is $-CH_3$, $-CH_2CH_3$, or $-OCH_3$, $R_2$ is H, $-CH_3$, $-CH_2CH_3$ or $-OCH_3$, and $R_3$ is H, $-CH_3$, $-CH_2CH_3$ or $-OCH_3$, wherein if $R_1$ is $-CH_3$, then at least one of $R_2$ or $R_3$ is not H. In particular compounds, $R_1$ is $-OCH_3$. In particular compounds, $R_1$ is $-CH_2CH_3$. In particular compounds, $R_2$ is $-CH_3$. In particular compounds, $R_3$ is $-CH_3$. Specific compounds are:

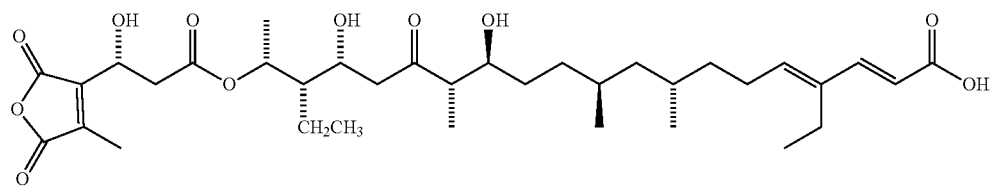 [SMILES: CCC(/C=C/C(=O)O)=C\CC[C@H](C)C[C@@H](C)CC[C@H](O)[C@H](C)C(=O)C[C@@H](O)[C@H](CC)[C@@H](C)OC(=O)C[C@@H](O)C1=C(C)C(=O)OC1=O]

-continued

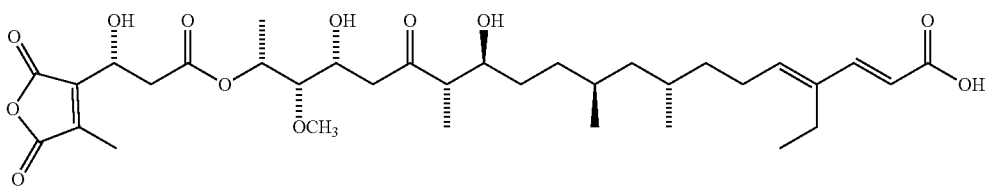 [SMILES: CCC(/C=C/C(=O)O)=C\CC[C@H](C)C[C@@H](C)CC[C@H](O)[C@H](C)C(=O)C[C@@H](O)[C@H](OC)[C@@H](C)OC(=O)C[C@@H](O)C1=C(C)C(=O)OC1=O]

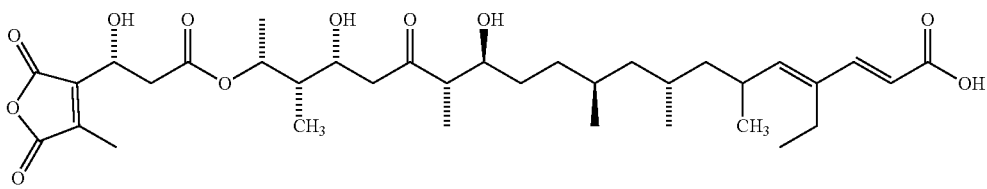

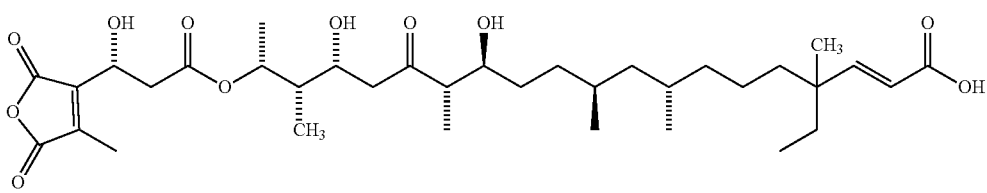

In particular, the compound may have $R_1$ as —$CH_2CH_3$, $R_2$ as —$CH_3$ and $R_3$ as —$CH_3$.

In another embodiment, there is provided a method of treating a SHP2-related cancer in a subject comprising contacting a SHP2-related cancer cell with tautomycetin or an analog thereof. The SHP2-related cancer may be other than colorectal cancer. The SHP2-related cancer may be other than leukemia. Also provide are methods for treating inflammatory diseases such as autoimmune disease, trauma, sepsis, acute pancreatitis, acute respiratory distress syndrome, ischemia reperfusion injury, cardiovascular disease, chemo-, radio- or cytokine therapy-induced inflammation, or burns. The analog may be TTN D1. The analog may have the formula:

—$CH_2CH_3$ or —$OCH_3$, wherein if $R_1$ is —$CH_3$, then at least one of $R_2$ or $R_3$ is not H. The may further comprise contacting said cancer cell with a second anti-cancer therapy, such as radiotherapy, chemotherapy, immunotherapy, chemotherapy or gene therapy. The cancer may be multi-drug-resistant, recurrent or metastatic. The subject may be a human. The method may further comprise assessing a cancer cell from said subject for a mutation in SHP2.

In still further embodiment, there is provided a method of treating Noonan syndrome comprising administering to a subject tautomycetin or an analog thereof. The subject may be treated with tautomycetin. The analog may be TTN D1. The analog may have the formula:

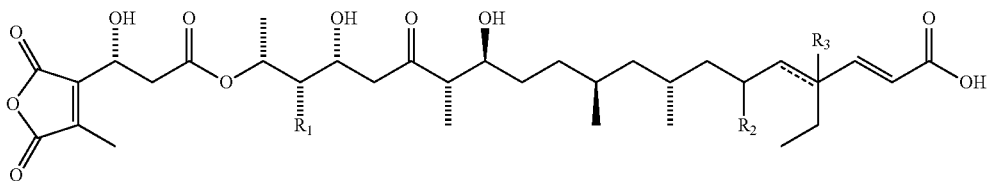

wherein $R_1$ is —$CH_3$, —$CH_2CH_3$, or —$OCH_3$, $R_2$ is H, —$CH_3$, —$CH_2CH_3$ or —$OCH_3$, and $R_3$ is H, —$CH_3$,

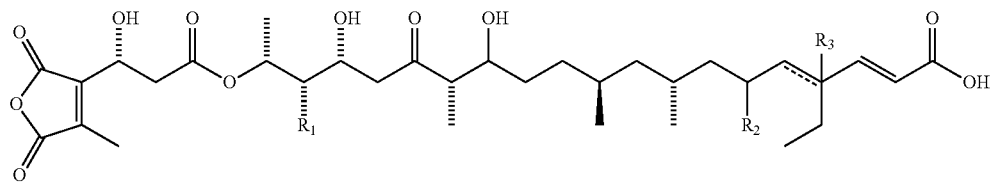

wherein $R_1$ is —$CH_3$, —$CH_2CH_3$, or —$OCH_3$, $R_2$ is H, —$CH_3$, —$CH_2CH_3$ or —$OCH_3$, and $R_3$ is H, —$CH_3$, —$CH_2CH_3$ or —$OCH_3$, wherein if $R_1$ is —$CH_3$, then at least one of $R_2$ or $R_3$ is not H. The method may further comprise assessing a cell from said subject for a mutation in SHP2.

In still yet another embodiment, there is provided a method or treating Leopard syndrome comprising administering to a subject tautomycetin or an analog thereof. The subject may treated with tautonycetin. The analog may be TTN D1. The analog the may have the formula:

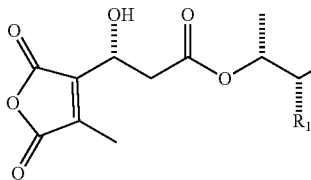

wherein $R_1$ is —$CH_3$, —$CH_2CH_3$, or —$OCH_3$, $R_2$ is H, —$CH_3$, —$CH_2CH_3$ or —$OCH_3$, and $R_3$ is H, —$CH_3$, —$CH_2CH_3$ or —$OCH_3$, wherein if $R_1$ is —$CH_3$, then at least one of $R_2$ or $R_3$ is not H. The method may further comprise assessing a cell from said subject for a mutation in SHP2.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(FIG. 1A) Diacid and anhydride forms of (FIG. 1B) TTM, TTN, and the engineered analog TTN D-1.

(FIG. 4A) TTN abrogated the GM-CSF induced ERK1/2 activation in macrophage progenitors. (FIG. 4B) $^3$H-thymidine incorporation assay of transduced, sorted bone marrow LDMNCs in the presence of GM-CSF 1 ng/mL+/−2 μM TTN, (two independent experiments, cultures plated in triplicate, *p=0.02 for SHP2/E76K in 2 μM TTN vs. SHP2/E76K in DMSO), (FIG. 4C) Transduced, sorted bone marrow LDMNCs plated into methylcellulose-based colony assays in GM-CSF 1 ng/mL+/−2 μM TTN, colony morphology (CFU-GM or CFU-M) was assessed by light microscopy, n=2, *p=0.03 for SHP2/E76K CFU-M in 2 μM TTN vs. SHP2/E76K CFU-M in DMSO.

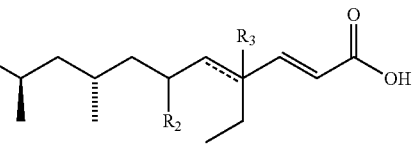

Figure 5:
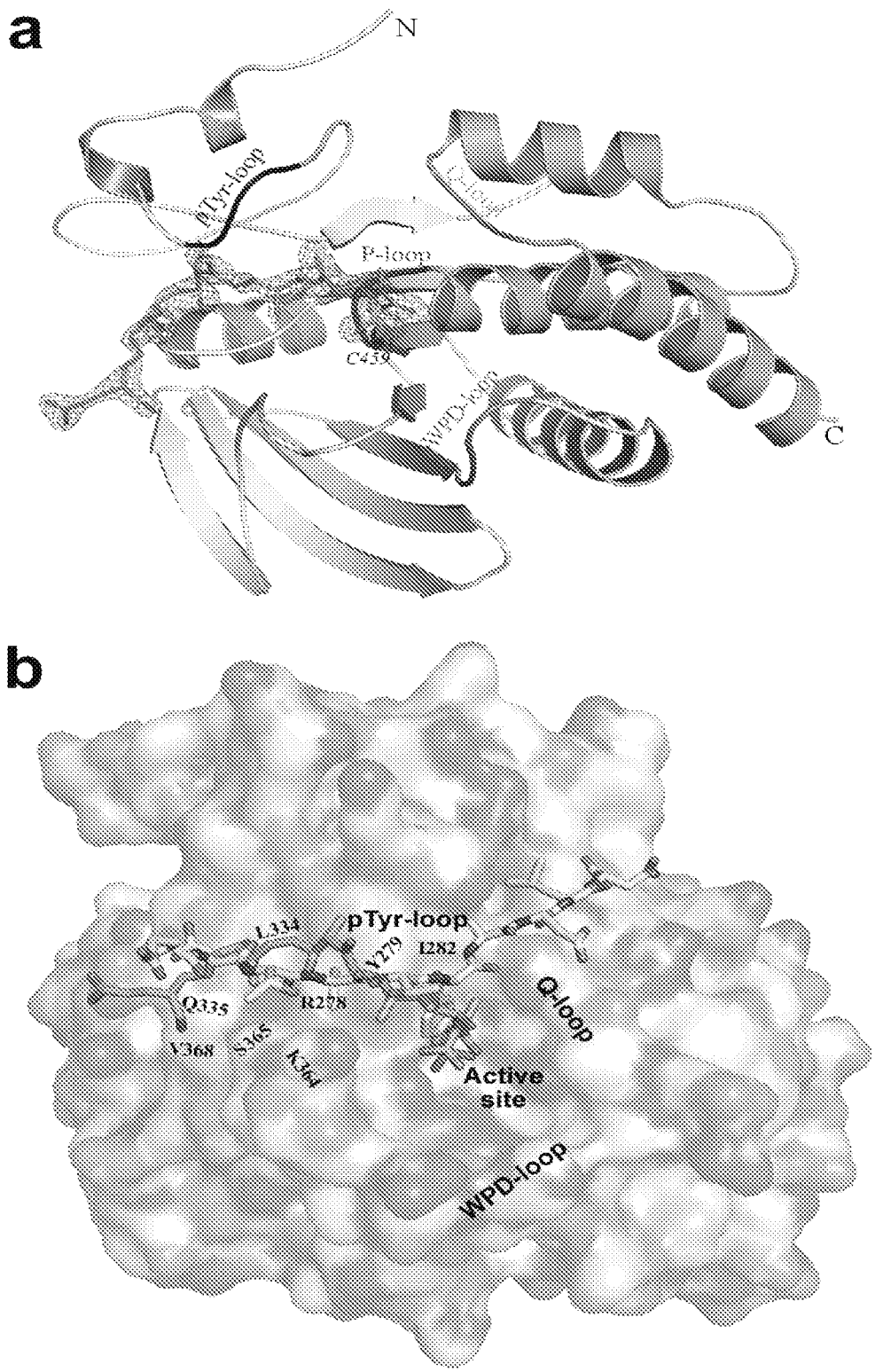

FIGS. 5A-B. Structure of TTN D-1 bound SHP2. (FIG. 5A) Cartoon diagram of SHP2 catalytic domain in complex with TTN D-1. α-helices and β-strands are colored in magenta and yellow, respectively. The P-loop is shown in red, the WPD loop in green, pTyr loop in blue, and Q loop in cyan. TTN D-1 is shown in stick model with its 2Fo–Fc electron density map contoured at 1.0 σ. (FIG. 5B) Binding mode comparison between SHP2.TTN D-1 and SHP1.pTyr peptide substrate. The structure of SHP1.peptide (PDB accession #: 1FPR) was superimposed onto our structure of SHP2.TTN D-1. The peptide (EDILTpYADLD) (yellow) and TTN D-1 (green) are shown in stick model.

Figure 6:
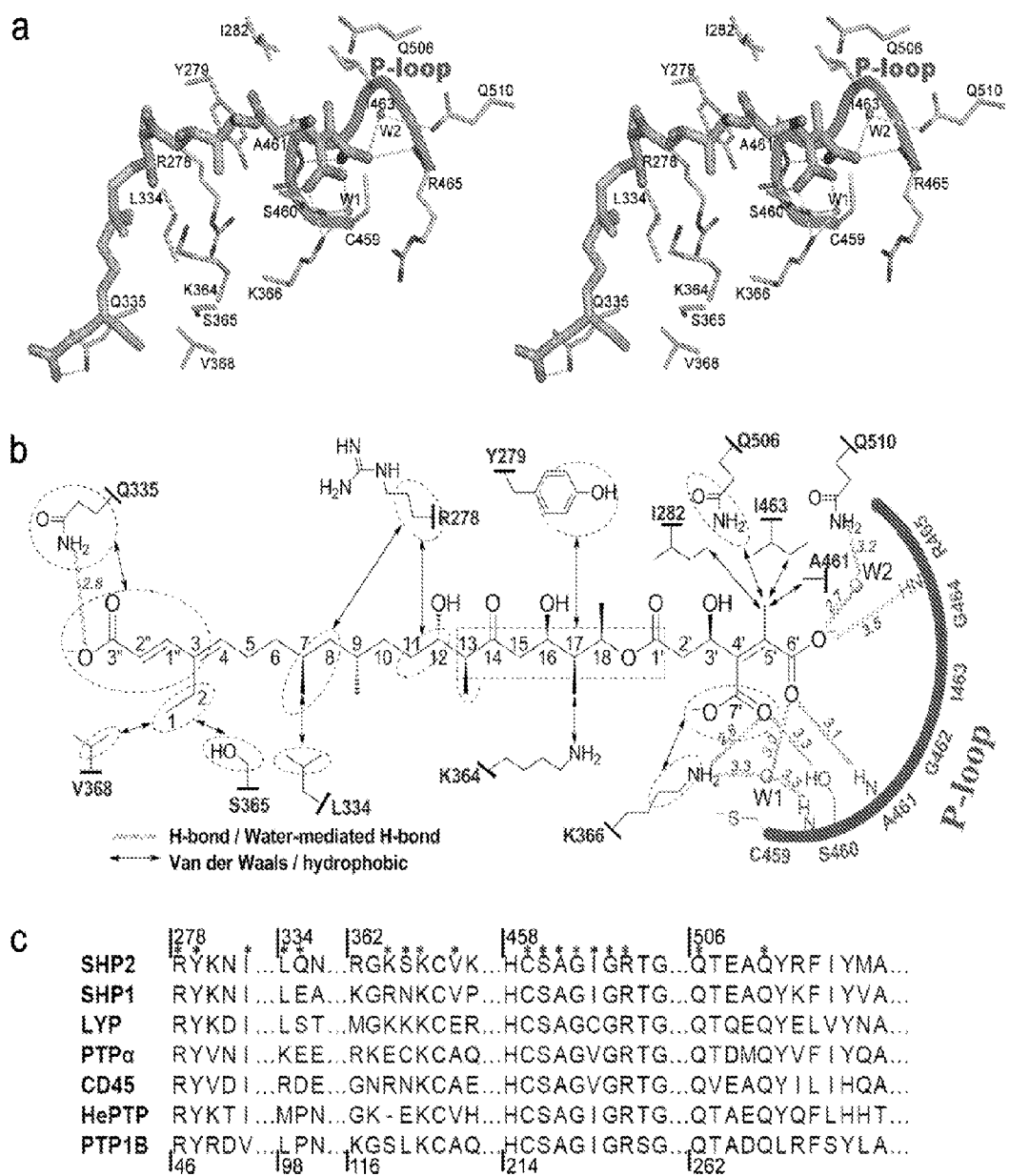

FIGS. 6A-C. Interaction between SHP2 and TTN D-1. (FIG. 6A) Stereo view showing interactions between TTN D-1 and SHP2. TTN D-1 (green carbon) and interacting residues in SHP2 (cyan carbon) are represented in stick model, and P-loop is depicted in red cartoon. Yellow dash lines represent H-bond interactions. (FIG. 6B) Interaction diagram of TTN D-1 and SHP2. (FIG. 6C) Amino acid sequence alignment of 7 human PTPs for which selectivity data were obtained for TTN and TTN D-1. Residues involved in the interaction with TTN D-1 revealed by our structure are marked by *; Sequence numbers in SHP2 and PTP1B are labeled at the top and bottom, respectively.

Figure 7:
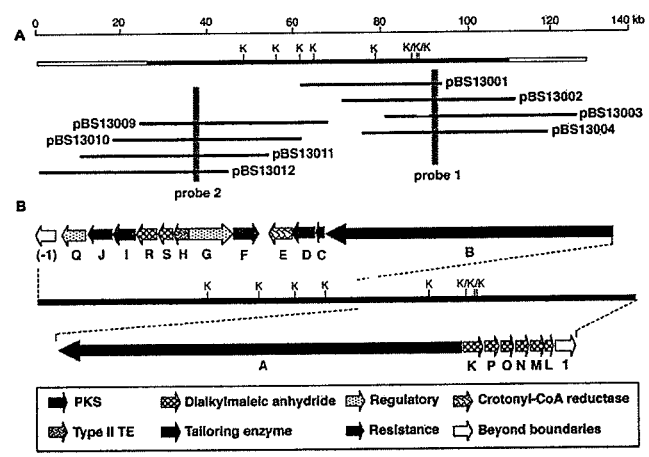

FIGS. 7A-B. (FIG. 7A) Restriction map of the 140 kb DNA region from *S. griseochromogenes* harboring the entire ttn gene cluster as represented by eight overlapping cosmids. Solid black bar indicates sequenced DNA region. (FIG. 7B) Genetic organization of the ttn gene cluster. Proposed functions for individual orfs are coded with various patterns and summarized in Table 1. K, KpnI.

Figure 8:
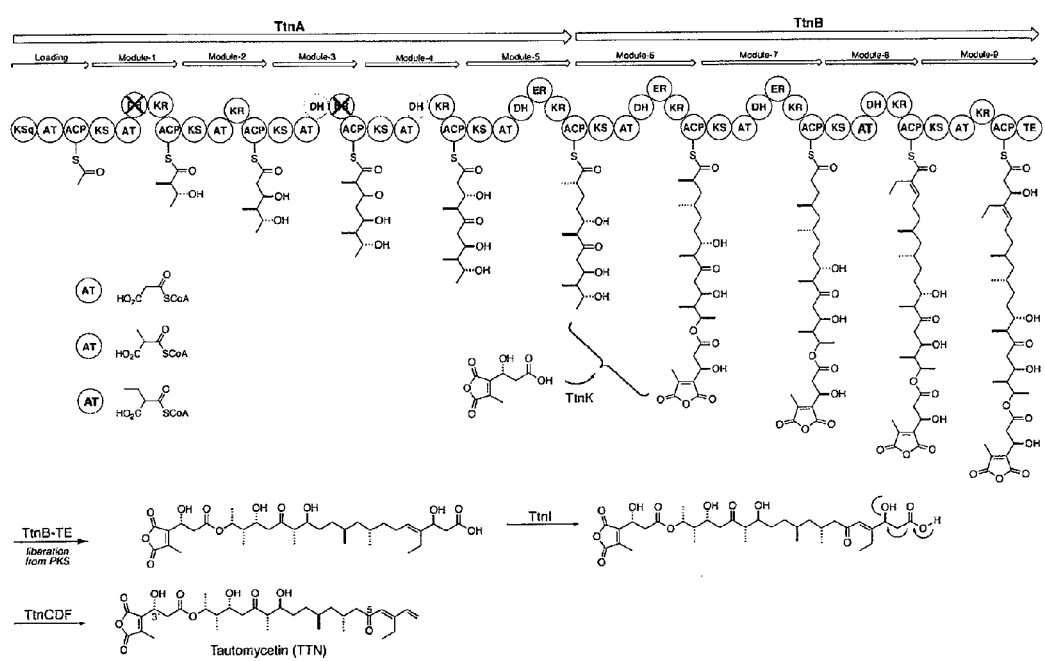

FIG. 8. Deduced module and domain organization of TtnA and TtnB PKSs and a linear model for TTN biosynthesis featuring the TTN PKS templated assembly of the TTN polyketide backbone featuring various starter and extender units, coupling of the dialkylmaleic anhydride to the elongating polyketide intermediate prior its reaching to full length, and other key tailoring steps. The AT domains are coded with various patterns to highlight their substrate specificity, "X" marks domains predicted to be inactive, and dotted circles indicate intact domains whose activities appear to be unnecessary. AT, acyl transferase; ACP, acyl carrier protein; KS, ketosynthase; DH, dehydratase; KR, ketoreductase; ER, enoylreductase; TE, thioesterase.

Figure 9A:
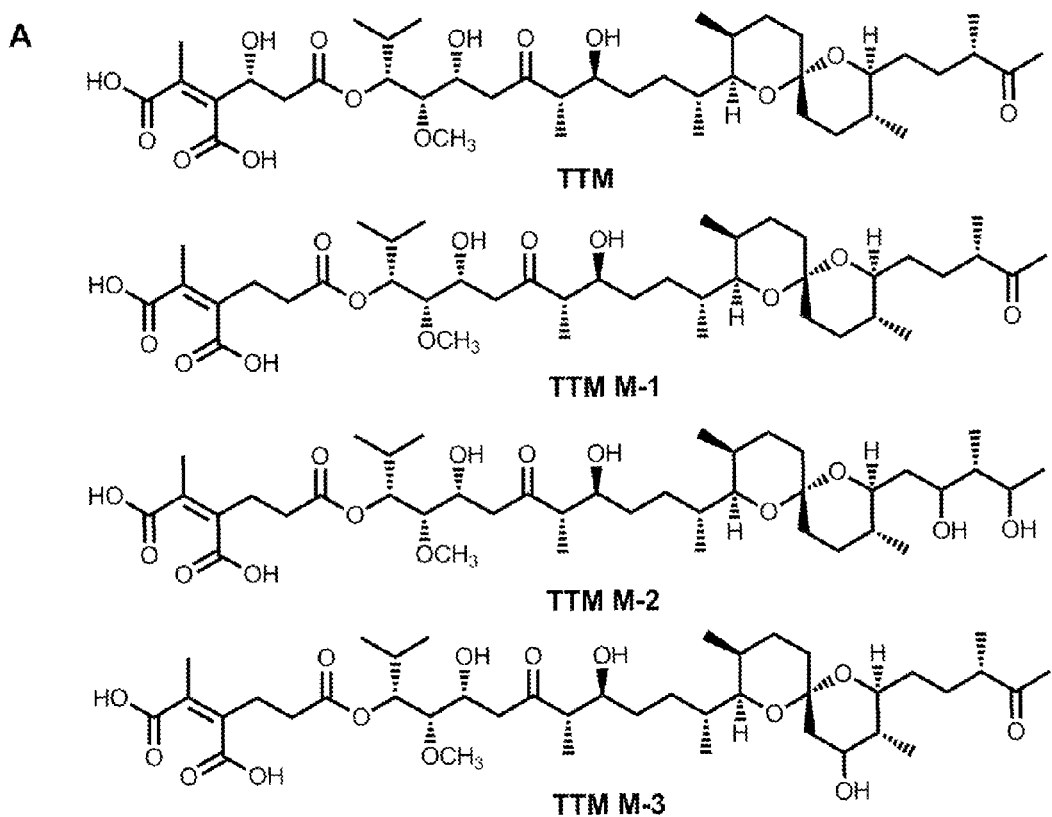
Figure 9B:
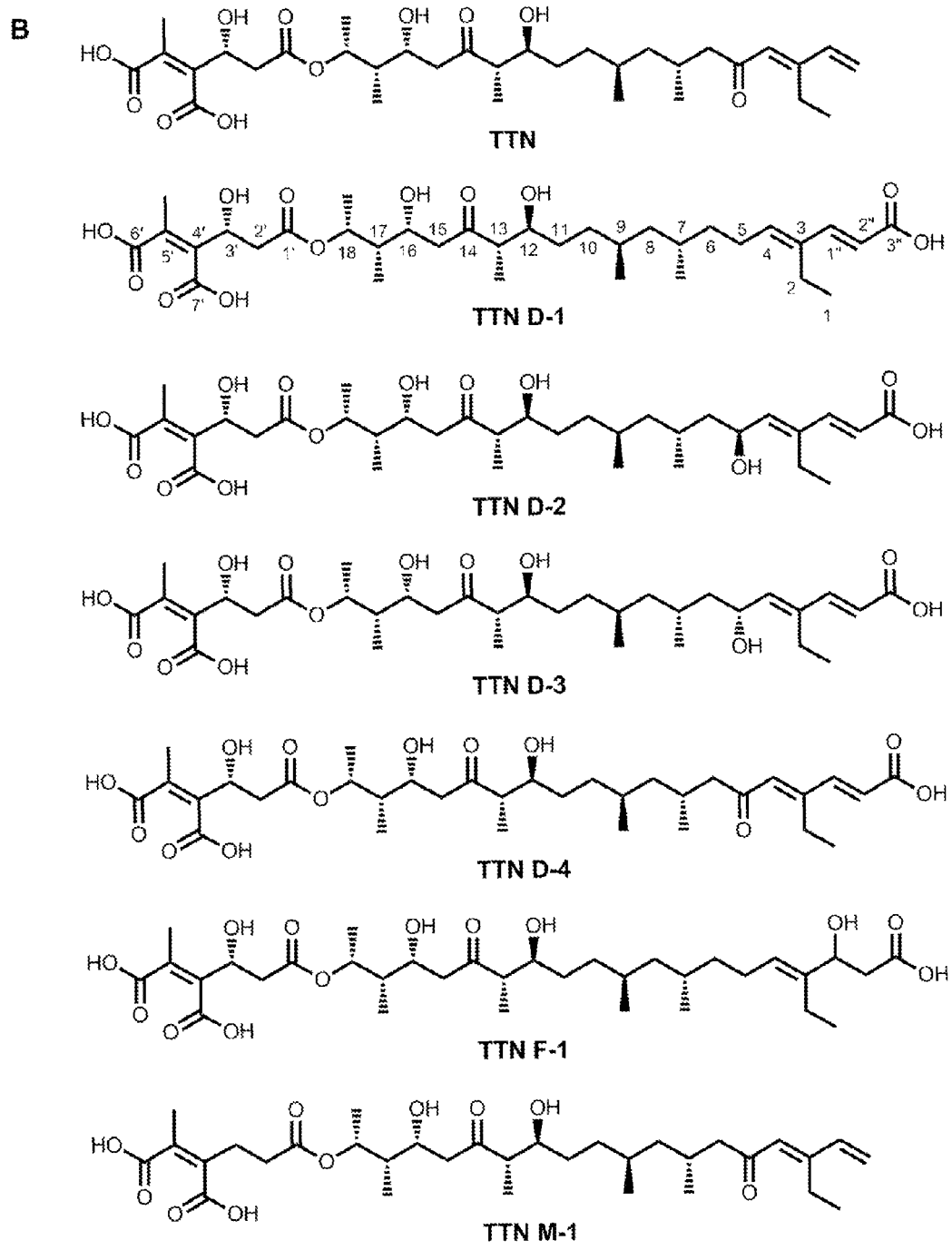

FIG. 9. Structures of TTN and TTM, along with nine engineered analogs featuring the TTN and TTM scaffolds.

Figure 10:
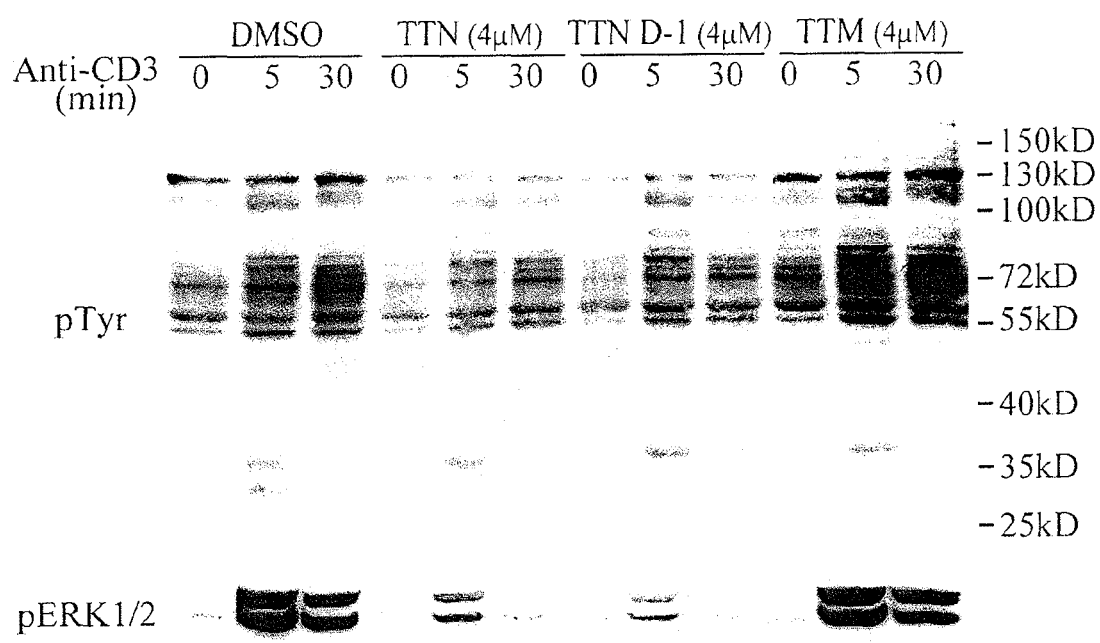

FIG. 10. Effect of TTN and TTN D-1 on TCR-mediated signaling in Jurkat T cells at a higher compound concentration (Related to FIG. 3). Cells were pretreated with 4 mM TTN, TTN D-1, or TTM for 2 hours and stimulated with 10 mg/mL anti-CD3 antibody. Cell lysates were immunoblotted with anti-pTyr and anti-phospho-ERK1/2 antibodies for total tyrosine phosphorylation and ERK1/2 activity.

Figure 11:
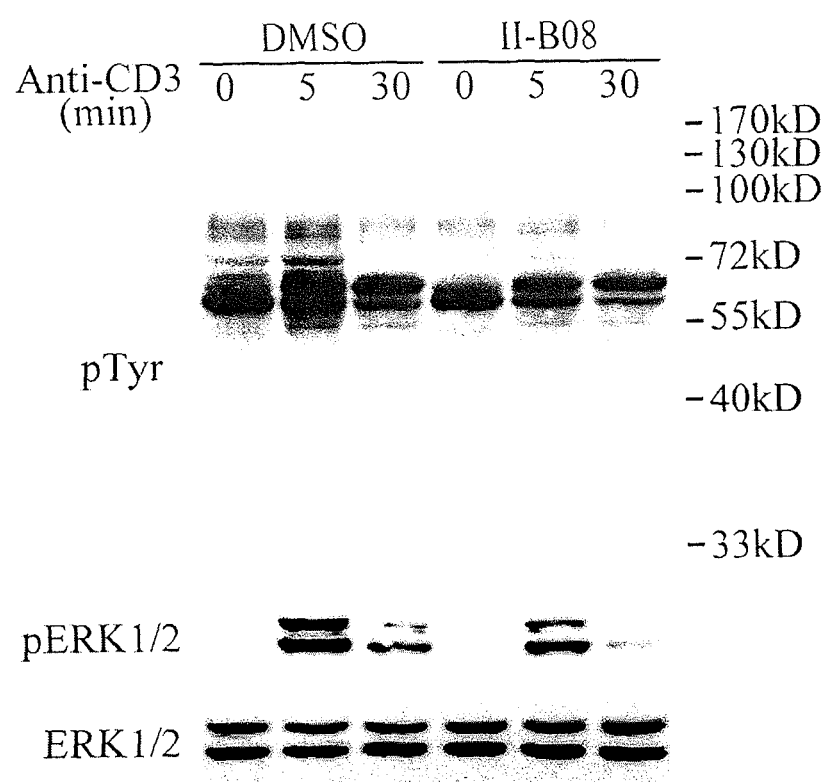

FIG. 11. Effect of SHP2 inhibitor II-B08 on TCR-mediated signaling in Jurkat T cells. Cells were pretreated with DMSO or 10 mM II-B08 for 60 min and stimulated with 10 mg/mL anti-CD3 antibody. Cell lysates were immunoblotted with anti-pTyr for total tyrosine phosphorylation and with anti-phospho-ERK1/2 and anti-ERK1/2 for activated ERK1/2 and total ERK1/2 respectively.

DETAILED DESCRIPTION OF THE INVENTION

In an effort to identify novel SHP2 inhibitors and to search for TTN's cellular target(s), the inventors screened a natural product library of TTN, TTM, and nine engineered analogs featuring the TTN and TTM scaffolds against SHP2 as well as a panel of other PTPs. TTN and its engineered analog TTN D-1 (FIGS. 1A-B), but not TTM, were found to inhibit the activity of SHP2. They showed that TTN and TTN D-1 block TCR-mediated tyrosine phosphorylation and ERK1/2 activation as well as activating SHP2-induced hematopoietic progenitor hyperproliferation and monocytic differentiation. Moreover, they determined the X-ray crystal structure of SHP2 with TTN D-1 bound to its active site. Together with the biochemical data, this structure supports the notion that SHP2 is a cellular target for TTN and provides molecular insights upon which novel therapeutics targeting SHP2 can be developed based on the TTN scaffold for multiple cancers and immunosuppression. These and other aspects of the invention are discussed in detail below.

I. Tautomycetin and Analogs Thereof

Tautomycetin (TTN), originally isolated from *Streptomyces griseochromogenes* in 1989, is structurally similar to tautomycin (TTM) (FIGS. 1A-B) (Cheng et al., 1989; Cheng et al., 1987). Both polyketides were initially described as antifungal antibiotics capable of inducing morphological changes in leukemia cells. More importantly, both compounds were found to specifically inhibit the protein phosphatases (PPs) PP1 and PP2A.3,4 PP1 and PP2A are two of the four major serine/threonine PPs that regulate an array of cellular processes including, but not limited to, cell cycle progression, gene expression, calcium transport, muscle contraction, glycogen metabolism, phototransduction, and neuronal signaling (Sakoff and McCluskey, 2004; Honkanen and Golden, 2002). Many human diseases are characterized by an altered interplay between phosphatases and kinases, and thus the selective inhibition of PP1 and PP2A has been proposed to be an attractive goal for rational anticancer drug design (McCluskey et al., 2002). For instance, TTN has been suggested as a potential drug for colorectal cancer because of its regulation of Raf-1 activity through inhibition of PP1 and PP2A in a cell-type-specific manner (Lee et al., 2006). PP1 and PP2A inhibition by TTM and TTN heightens interest in the possible application of combinatorial biosynthesis methods as an integral tool for the discovery of new therapeutics based on the anhydride-capped polyketide scaffold of TTM and TTN.

In contrast to other naturally occurring PP1 and PP2A inhibitors, such as okadaic acid (OA) (Bialojan and Takai, 1988), fostriecin (Roberge et al., 1994), cantharidin (Li and Casida, 1992), microcystin-LR (MacKintosh et al., 1990), and calyculin-A (Ishihara et al., 1989), TTM and TTN exhibit a high degree of PP1 selectivity. TTM inhibits PP1 and PP2A with $IC_{50}$ values of 22-32 nM while showing a slight preference for PP1 (MacKintosh et al., 1990; Colby et al., 2003; Oikawa, 2002; Sugiyama et al., 1996; Takai et al., 1995). Conversely, TTN preferentially inhibits PP1 by a factor of about 40-fold relative to PP2A ($IC_{50}$=1.6 nM for PP1 versus 62 nM for PP2A) (Mitsuhashi et al., 2001). By virtue of its high selectivity for PP1 inhibition, TTN represents not only an interesting drug lead but also a powerful biochemical tool with which to elucidate the roles of PP1 in various biological pathways.

Despite their similarities of structure and activity, TTN, but not TTM, has been identified as a potent immunosuppressor of activated T cells in organ transplantation (Shim et al., 2002). Inhibition of T cell proliferation by TTN was observed at concentrations 100-fold lower than those needed to achieve maximal inhibition by cyclosporine A (CsA). CsA and FK506 exert their pharmacological effects by binding to the immunophilins; the resulting complex binds to and inhibits the Ser/Thr phosphatase calcineurin albeit with potentially deleterious effects due to the physiological ubiquity of calcineurin (Flanagan et al., 1991; Bierer et al., 1990; Hong and Kahan, 2000). TTN exerts immunosuppressive activity in a manner completely different from those of CsA and FK506 by blocking tyrosine phosphorylation of intracellular signal mediators downstream of the Src tyrosine kinases in activated T cells. This leads to cell-specific apoptosis due to cleavage of Bcl-2, caspase-9, caspase-3, and poly(ADPribose) polymerase, but not caspase-1 (Shim et al., 2002; Chae et al., 2004). The activated T cell specificity of TTN thus suggests this unique polyketide as a significant lead in the search for immunosuppressive drugs superior to CsA and FK506.

The gross structure of TTN was deduced by chemical degradation and spectroscopic analysis (Cheng et al., 1990), and the relative and absolute stereochemistry was established by comparison of spectral data for degradation products of TTN with those of synthetic fragments (Dai et al., 1996). Both TTM and TTN exist as a tautomeric mixture consisting of two interconverting anhydride and diacid forms in approximately a 5:4 ratio under neutral conditions (Cheng et al. 1987; Cheng et al., 1990a; Cheng et al., 1990b). Since the major structural differences between TTM and TTN reside in the region distal to the dialkylmaleic anhydride, it has been proposed that these differences might be responsible for variations in their PP1 selectivity (Oikawa, 2002; Nishiyama et al., 1996; Sheppeck et al., 1997; Takai et al., 2000).

The inventors have now described analogs of TTN designated herein as TTN D-1, TTN D-2, TTN D-3, and TTN D-4. These analogs were created by inactivating the ttnd gene. These genes encode L-carnitine dehydratase and UbiD family decarboxylase enzymes, respectively. Each of these analogs is modified, with respect to TTN, at the right end of the molecule, where TTN has a terminal methylene group, and the analogs each have a terminal carboxy group with four of the five also being changed in the carbonyl group at C5.

A. TTN D-1

Absolute yield: 17 mg from 40 L of fermentation broth of SB13013. Off-yellowish gum; $[\alpha]_D^{25}$=+20.0 (c 1.0, acetone); APCI-MS (negative mode) m/z 635 ([M-H]$^-$, 100); HR-MALDI-MS (positive mode) m/z 659.3412 [M+Na] (calc'd for $C_{34}H_{52}O_{11}Na$, 659.3402, 1.58 ppm error); IR 3422, 2930, 1766, 1706, 1621, 1515, 1456, 1364, 1259, 1222, 1177, 1089, 1062, 1029, 985, 907, 852, 764, and 731 cm$^{-1}$.

B. TTN D-2

Absolute yield: 30 mg from 40 L of fermentation broth of SB13013. Off-yellowish gum; $[\alpha]_D^{25}$=+12.0 (c 2.0, acetone); APCI-MS (negative mode) m/z 651 ([M-H]$^-$, 100); HR-ESI-MS (negative mode) m/z 651.3400 [M-H]$^-$ (calc'd for $C_{34}H_{51}O_{12}$, 651.3375, 3.83 ppm error); IR 3407, 2931, 1830, 1765, 1703, 1621, 1456, 1365, 1260, 1223, 1179, 1032, 986, 957, 907, 854, and 732 cm$^{-1}$.

C. TTN D-3

Absolute yield: 12 mg from 40 L of fermentation broth of SB13013. Off-yellowish gum; $[\alpha]_D^{25}$=+21.8 (c 1.0, acetone); APCI-MS (negative mode) m/z 651 ([M-H]$^-$, 100); HR-ESI-MS (negative mode) m/z 651.3399 [M-H]$^-$ (calc'd for $C_{34}H_{51}O_{12}$, 651.3375, 3.68 ppm error); IR 3406, 2961, 1830, 1765, 1703, 1621, 1456, 1365, 1260, 1223, 1179, 1040, 985, 956, 908, 855, and 732 cm$^{-1}$.

D. TTN D-4

Absolute yield: 4 mg from 40 L of fermentation broth of SB13013. Off-yellowish gum; $[\alpha]_D^{25}$=+12.0 (c 2.0, acetone); APCI-MS (negative mode) m/z 649 ([M-H]$^-$, 100); HR-ESI-MS (negative mode) m/z 649.3239 [M-H]$^-$ (calc'd for $C_{34}H_{49}O_{12}$, 649.3219, 3.15 ppm error); IR 3416, 2966, 1829, 1765, 1704, 1625, 1581, 1457, 1378, 1261, 1181, 1090, 1033, 986, 957, 908, and 732 cm$^{-1}$.

E. Analogs

A generic structure for the D-1 to D-4 molecules is shown below:

wherein X is O, OH or H, and R is $(CH_2)$—COOH or $CH(OH)CH_2$—COOH. Further variants are contemplated by the following structure:

wherein $R_1$ is —$CH_3$, —$CH_2CH_3$, or —$OCH_3$, $R_2$ is H, —$CH_3$, —$CH_2CH_3$ or —$OCH_3$, and $R_3$ is H, —$CH_3$, —$CH_2CH_3$ or —$OCH_3$, wherein if $R_1$ is —$CH_3$, then at least one of $R_2$ or $R_3$ is not H. This group of variants are designed in view of the crystal structure defined interaction of the TTN-D1 analog binding to SHP2. In fact, TTN-D1 itself fits and complements the surface of SHP2 very well. However, modifications at three positions are predicted to increase the Van der waals interactions. Specific variants are illustrated below:

The above molecule can be produced by replacing the AT of module-1 with an ethyl Molony-CoA specific AT such as from the AT in module-8 (FIG. 8).

Figure 3:
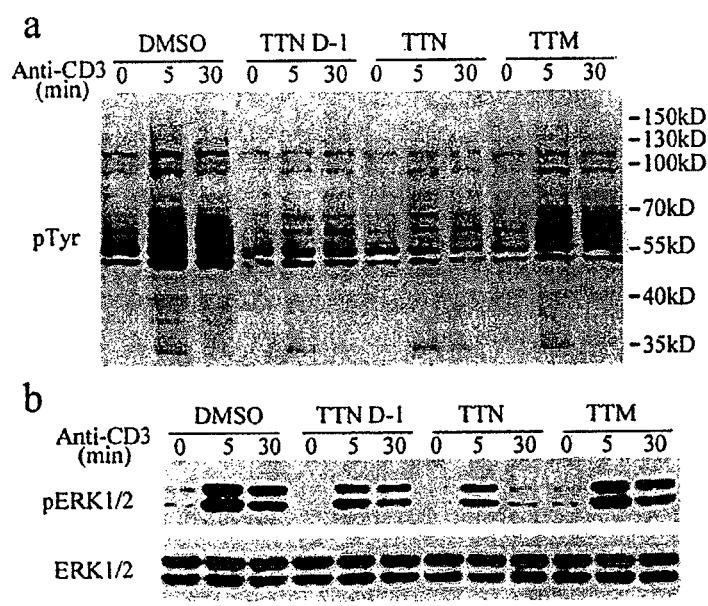
FIGS. 3A-B. Effects of TTN and TTN D-1 on anti-CD3 induced tyrosine phosphorylation and ERK1/2 activation. Anti-CD3 induced tyrosine phosphorylation (FIG. 3A) and ERK1/2 activation (FIG. 3B) in Jurkat T cells.

The above molecule can be produced by replacing the AT of module-1 (FIG. 8) with an ethyl methoxymalony-CoA specific AT such as from the AT in module-1 of the tautomycin gene cluster (see FIG. 3, JBC, 2008, 283, 28607-28617).

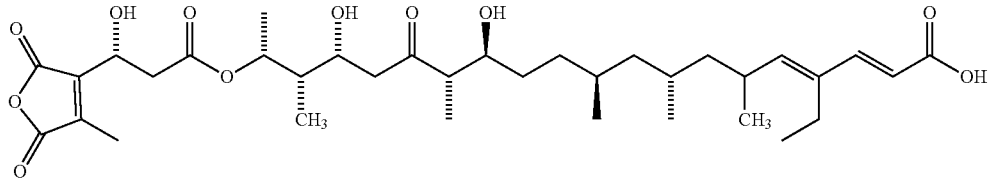 [SMILES: CCC(/C=C/C(=O)O)=C\C(C)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

The above molecule can be produced by replacing the AT of module-7 (FIG. 8) with a methyl Molony-CoA specific AT such as the AT in module-6 (FIG. 8).

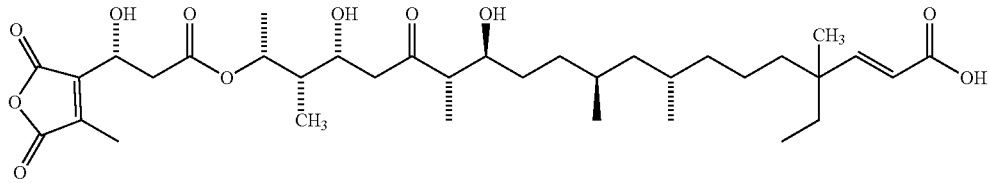 [SMILES: CCC(C)(/C=C/C(=O)O)CCC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

The above molecule can be produced by replacing the AT of module-8 (FIG. 8) with a methyl Molony-CoA specific AT such as the AT in module-6 (FIG. 8).

II. Characterization of the TTN Gene Cluster

Previously, the inventor reported the cloning and sequencing of the ttn gene cluster including a determination of its boundaries, along with the development of an expedient genetic system for S. griseochromogenes (Li et al., 2009). The bioinformatics analysis of the ttn cluster and a proposal for TTN biosynthesis were also presented along with a the genetic characterization of the TTN pathway to support the proposed pathway (Li et al., 2009). Integral to this work was the elucidation, enabled by accurate assignment of the ttn cluster boundaries, of all genes responsible for dialkylmaleic anhydride biosynthesis. This report, combined with previous work on the ttm cluster, now enables rapid access to their biosynthetic gene cluster as well as genome mining of microorganisms for new dialkylmaleic anhydridecontaining natural products. A ΔttnM mutant was prepared, which produced the C-32 deshydroxy analogue TTN M-1.

A. Cloning and Sequencing

PCR and Southern analyses of which confirmed that the two loci, identified with probes 1 and 2, respectively, overlap (FIG. 7A). A total of 125 kb continuous DNA region was finally localized, 79 kb of which was ultimately sequenced on both strands. The overall G+C content for the sequenced region was 71.6%. The sequence was deposited in GenBank database under the accession number EUO35755. Twenty-one complete open reading frames (orfs) were identified, among which 19 were designated as ttn genes (FIG. 7B). Corresponding homologues and the proposed function of each ttngene product are summarized in Table 1. The deduced gene products include two large PKSs composed of a total of 10 modules, eight enzymes involved in dialkylmaleic anhydride biosynthesis, four tailoring enzymes, two regulatory proteins, and one resistance protein. While this work was in progress, a partial ttn cluster from Streptomyces sp. CK4412 was reported, which included 14 (i.e., spanning from ttnG to orf1) of the 21 orfs reported here; the cluster boundaries however were not determined (Choi et al., 2007). While not identical, the two clusters are highly homologous with protein amino acid sequences ranging from 97% to 99% identity.

TABLE 1

Deduced Functions of Open Reading Frames n the tautomycetin Biosynthetic Gene Cluster

| Gene | Size[a] | Proposed Function | Homologue[b] | Identity %/similarity % |
|---|---|---|---|---|
| orf(−1) | 262 | Transposase | MUL_2441 (YP_906264) | 32/42 |
| | | Upstream boundary of the ttn cluster | | |
| ttnQ | 472 | Transciptional activator | StaR (BAC55205) | 13/19 |
| ttnJ | 560 | Multidrug transporter | RHA1_ro04399 (YP_704343) | 49/53 |
| ttnI | 449 | Cytochrome P450 | EryF (1Z8Q_A) | 30/43 |
| ttnR | 470 | Dehydratase | PrpD (2HP3_A) | 24/38 |
| ttnS | 272 | Unknown | PFL_4035 (YP_261132) | 27/39 |
| ttnH | 259 | Thioesterase | PiKAV (AAC69333) | 42/53 |
| ttnG | 926 | Regulatory protein | ThcG (AAD28307) | 33/46 |
| ttnF | 505 | L-carnitine dehydratase | caiB (1Xk7_B) | 12/24 |
| ttnE | 444 | Crotonyl-CoA reductase | CCr (AAA92890) | 75/84 |
| ttnD | 485 | UbiD family decarboxylases | UbiD (21DB_A) | 24/36 |
| ttnC | 209 | Flavoprotein decarboxylase | VdcB (AAD28781) | 57/71 |
| ttnB | 7576 | PKS modules 6-9 | | |
| ttnA | 9528 | PKS loading module and modules 1-5 | | |

TABLE 1-continued

Deduced Functions of Open Reading Frames n the tautomycetin Biosynthetic Gene Cluster

| Gene | Size[a] | Proposed Function | Homologue[b] | Identity %/similarity % |
|---|---|---|---|---|
| ttnK | 465 | Esterase | PnbA (1QE3_A) | 29/44 |
| ttnP | 383 | CoA transferase | CaiB (1XVV_A) | 24/41 |
| ttnO | 309 | Citryl CoA lyase | Mtb CitE (1Z6K_A) | 24/37 |
| ttnN | 363 | Unknown | EhPf (AAN40895) | 37/52 |
| ttnM | 339 | Hydroxylase | Plav_0577 (YP_001411857) | 29/42 |
| ttnL | 185 | Unknown | Ybhb (1FUX_A) | 25/33 |
| | | Downstream boundary of the ttn cluster | | |
| orf1 | 507 | Polyprenyl phospho-mannosyltransferase | MppI (AAU34200) | 32/48 |

[a]Numbers are in amino acids.
[b]Given n parentheses are NCBI accession numbers.

The ttn gene cluster boundaries were defined by combining bioinformatics analysis and gene inactivation (FIG. 7B). For the upstream boundary, orf(−1) encodes a putative transposase. Given the improbable role of a transposase during TTN biosynthesis, orf(−1) most likely lies beyond the ttn cluster. Immediately downstream of orf(−1) is a putative regulatory gene, ttnQ. Inactivation of ttnQ, affording the mutant strain SB13001, completely abolished TTN production, establishing its indispensability for TTM biosynthesis. For the downstream boundary, orf1 encodes a putative polyprenyl phosphomannosyltransferase. Inactivation of orf1, affording mutant strain SB13002, had little impact on TTN production, excluding the involvement of orf1 in TTN biosynthesis. Immediately upstream of orf1 is ttnL, a homologue of ttmL that has been confirmed to be essential for dialkylmaleic anhydride biosynthesis, hence essential for TTN biosynthesis (Li et al., 2008).

B. Assignment of Gene Function

Two large orfs, ttnA and ttnB, that encode modular type I PKSs responsible were identified within the ttn cluster (FIGS. 7B and 8). The ttnA gene encodes the loading module and extension modules 1-5, whereas ttnB encodes extension modules 6-9 and has a C-terminal thioesterase domain for release of the full-length polyketide chain. Together, the TTN PKS of TtnA and TtnB consists of one loading module and nine extension modules and catalyzes nine rounds of decarboxylative condensation, using one malonyl CoA as a starter unit (loading module) and four malonyl CoA (modules 2, 4, 7, and 9), four methylmalonyl CoA (modules 1, 3, 5, and 6), and one ethylmalonyl CoA (module 8) as extender units, for initiation, elongation, and termination of the biosynthesis of the polyketide backbone of TTN (FIG. 8).

Domain functions were deduced by sequence homology to known PKS domains (Staunton and Weissman, 2001). The loading module contains a mutated ketosynthase (KSq), an acyltransferase (AT), and an acyl carrier protein(ACP) domain, and each of the nine extension modules is minimally characterized by ketosynthase (KS), AT, and ACP domains. All KS domains contain the CHH catalytic triad required for the decarboxylative condensation reaction. All the ACP domains feature the highly conserved signature motif of DSL, in which the serine residue acts as the site for 4'-phosphopantatheinylation, a posttranslational modification essential for polyketide biosynthesis by converting the apo-ACPs into the functional holo-ACPs. The choice of the loading module and the extender unit is dictated by the corresponding AT domains, for which the specificity is predicted on the basis of sequence comparison with ATs of known substrates.

The nine extension modules are also characterized with additional domains such as ketoreductase (KR), dehydratase (DH), and enoylreductase (ER) domains, the presence of which accounts for the reductive modification of the β-keto group of the growing polyketide intermediate during each cycle of elongation. Functional KR domains, featuring the conserved consensus sequence GxGxxGxxA associated with NADP(H) binding, are found for all extension modules, except for KR in extender module 3, which contains a 16-amino acid deletion in the catalytic domain and, therefore, is inactive. Functional DH domains, containing the conserved consensus sequence HxxxGxxxxP, are identified for modules 5, 6, 7, and 8, excluding the DH domain in module 1, which contains a YxxxGxxxxP motif and, therefore, is inactive. In addition, intact DH domains are also present in extension modules 3 and 4, although their activities appear to be unnecessary in these modules. Finally, functional ER domains, having the conserved sequence GxGxAAxxxA, are predicted for modules 5, 6, and 7 (FIG. 8).

The TE domain at the C-terminus of TtnB terminates polyketide biosynthesis by liberating the full-length polyketide intermediate from the TTN PKS biosynthetic machinery (FIG. 8). Finally, in addition to the chain-terminating TE domain embedded within TtnB, a discrete type II TE (TEII), TtnH, remote from TtnA and TtnB within the ttn gene cluster, was also identified. TtnH may serve as an "editing" enzyme for mis-primed or stalled TtnA or TtnB PKS during polyketide chain elongation.

To support the predicted PKS function, ttnA was inactivated by using the PCR targeting strategies. Cosmid pBS13014, in which a 422 by DNA region within the ttnA gene was replaced with the aac(3)IV/oriT cassette, as introduced into S. griseochromogenes. Apramycin-resistant and kanamycin-sensitive exconjugants were selected as double crossover recombinant mutants, named SB13003, for which the desired ΔttnA genotype was confirmed by PCR and Southern blot analysis. Fermentation of SB13003, with the wild-type strain as a positive control, followed by extraction and HPLC analysis revealed that inactivation of ttnA completely abolished TTN production, consistent with the indispensable role proposed for TtnA in TTN biosynthesis.

Comparison of the TTM and TTN biosynthetic gene clusters revealed eight conserved enzymes, TtnKLMNOPRS, strongly supporting the involvement of these genes in dialkylmaleic anhydride moiety biosynthesis (Li et al., 2008). These conserved orfs include (i) TtmO/TtnO, a putative citryl-CoA lyase; (ii) TtmP/TtnP, a putative CoA transferase; (iii) TtmR/TtnR, a putative dehydratase; (iv) TtmM/TtnM, a putative hydroxylase; (v) TtmK/TtnK, a putative esterase; (vi) TtmS/TtnS, a putative cyclase; (vii) TtmL/TtnL, a phosphatidylethanolamine-binding protein; and (viii) TtmN/TtnN, an apparently conserved hypothetical protein. The coordination of these enzymatic activities for biosynthesis of the dialkylmaleic anhydride moiety is postulated.

Selected genes (ttnM, ttnP, ttnR, and ttnS) were next inactivated to investigate their roles in dialkylmaleic anhydride, hence TTN biosynthesis. In each case, the target gene was replaced in vitro by the aac(3)IV/oriT cassette using the PCR targeting strategies, yielding a mutated cosmid. Upon introduction of the mutated cosmids into wild-type *S. griseochromogenes*, apramycin-resistant and kanamycin-sensitive double crossover recombinant strains were selected, for which the desired mutant genotypes were finally confirmed by PCR and Southern blot analyses. Assigned names for each mutant strain are SB13004 (ΔttnM), SB13005 (ΔttnP), SB13006 (ΔttnR), and SB13007 (ΔttnS), respectively. Additionally, genetic complementation experiments were carried out to eliminate the possibility of polar effects. Plasmids pBS13017, pBS13018, and pBS13019, containing intact ttnM, ttnP, and ttnR genes under the control of ErmE* promoter, were introduced into SB13004, SB13005, and SB13006, yielding SB13009, SB13010, and SB13011, respectively.

These recombinant strains were fermented alongside the wild-type strain as a positive control, and TTN production was examined by HPLC analysis of the fermentation extracts. All four gene inactivation mutant strains failed to produce TTN, firmly establishing the essential roles these genes play in TTN biosynthesis. Moreover, under no circumstances were TTN intermediates detected in the SB13005 (ΔttnP), SB13006 (ΔttnR), or SB13007 (ΔttnS) mutant strain, consistent with the proposed critical functions of ttnP, ttnR, or ttnS in dialkylmaleic anhydride biosynthesis. TTN production was partially restored upon expression of a functional copy of the targeted gene in trans position, as exemplified by ttnP (pBS13022) and ttnR (pBS13023) to SB 13005 (ΔttnP) and SB13006 (ΔttnR), respectively, to approximately 60% (SB13010) and 80% (SB13011) of the levels observed for the wild-type strain. The tmcD gene, the homologue of ttnP from the recently reported partial ttn cluster from S. sp. CK4412, has also been inactivated. The resultant ΔtmcD mutant strain also abolished TTN production, although no in vivo complementation to ΔtmcD was reported (Choi et al., 2007). In contrast, the SB13004 (ΔttnM) mutant strain accumulated four new compounds, with TTN M-1 being the predominant product. Introduction of the ttnM expression construct (pBS13021) into SB13004 partially restored TTN production to approximately 30% (SB13009) of the level seen for the wild-type strain with concomitant disappearance of the four new compounds. The latter result suggests that TtnM-mediated oxidation likely precedes convergence of the dialkylmaleic anhydride and polyketide halves of TTN. This is contrary to earlier postulates invoking TtnMmediated oxidation as the last step in TTN biosynthesis (FIG. 3) (Choi et al., 2007).

The identity of TTN produced by the *S. griseochromogenes* wild-type and recombinant strains was confirmed by MS and $^1$H and $^{13}$C NMR analysis; all spectra were identical to those of authentic TTN. The four new compounds produced by SB13004 were found to have UV-vis spectra identical to that of TTN, suggesting they all contain the dialkylmaleic anhydride moiety. The dominant compound, TTN M-1, was isolated, and its structure established by MS, UV-vis, $^1$H NMR, $^{13}$C NMR, and other 2D NMR methods as that of C3' deshydroxy-TTN. The three minor products of SB 13004 fermentation were analyzed by HLPC-MS. Molecular weights for TTN M-2, TTN M-3, and TTN M-4 were found to be 576.4, 606.4, and 606.4 amu, respectively, but detailed structural elucidation was not pursued in the current study due to their minute production titers.

Compared to the nascent polyketide chain released by the TtnB terminal TE domain, the mature polyketide moiety of TTN has the following two varying functionalities: (i) a carbonyl group at C-5 position and (ii) the terminal diene structure. While TtnI (a cytochrome P450 hydroxylase) serves as a candidate for C-5 oxidation, the terminal diene structure calls for the nascent polyketide chain to undergo decarboxylation and dehydration upon release from TtnB. The latter are probably catalyzed by TtnC (a putative flavoprotein decarboxylase) or TtnD (a putative UbiD family decarboxylases) and TtnF (a putative L-carnitine dehydratase), respectively. The exact timing of carbonyl group formation, decarboxylation, and dehydration, however, needs to be determined by further experiments.

Regulatory and resistance proteins have also been unveiled upon sequencing the complete ttn cluster. The two regulatory genes identified within the ttn cluster are ttnG, which codes for a protein with 33% identity to the regulatory protein ThcG (AAD28307) from *Rhodococcus erythropolis*, and ttnQ, which codes for a protein with 41% identity to SareDRAFT_1231 (ZP_01648842) from *Salinispora arenicola* CNS205. Both TtnG and TtnQ belong to the LuxR family of transcription factors with the classical LuxR helix-turn-helix (HTH) motif proximal to each protein's C-terminus. Typically activated for DNA binding through associations with autoinducers such as N-(3-oxohexanoyl)-L-homoserine lactone, the LuxR homologues TtnG and TtnQ are intriguing since both lack an N-terminal autoinducer binding domain (Sitnikov et al., 1996). Additionally, TtnG contains a TTA leucine codon suggesting a possible dependence on bldA, the structural gene of tRNA$^{UUA}$ (Leskiw et al., 1993).

Identification of TtnG and TtnQ as regulatory protein candidates may have a bearing on metabolic engineering efforts to improve TTN titers. As described in the determination of the cluster boundary section, inactivation of ttnQ, affording mutant strain SB13001, completely abolished TTN production, a finding that agrees with TtnQ being a positive regulator. TTN production was partially restored to approximately 70% (SB13008) of the level seen for the wild-type strain upon introduction of the ttnQ expression construct (pBS13020) into SB13001. Similarly, tmcN, the homologue of ttnG from the recently appearing partial ttn cluster from S. sp. CK4412, has also been inactivated. The resultant ΔtmcN mutant strain completely lost its ability to produce TTN, as would be expected for a pathway-specific positive regulator (Hur et al., 2008).

Common resistance mechanisms by which microorganisms protect themselves from the potentially deleterious effects of their own bioactive natural products include intracellular compound modifications or sequestration, modification of the normally sensitive target so as to render it impervious to the effects of the natural product, and extracellular export (Hopwood, 2007). Within the ttn cluster one such transporter protein candidate coded for by ttnJ was found. This putative resistance protein, TtnJ, was found to have 49% identity to the cytoplasmic membrane multidrug transporter RHA1_ro04399 (YP_704343) from *Rhodococcus* sp. RHA 1. It thus appears that *S. griseochromogenes* may derive TTN resistance via an export mechanism, although further studies are warranted to confirm this postulate.

C. Engineering and Biosynthesis

In certain embodiments of this invention, the TTN biosynthetic gene cluster will be introduced into a vector or vectors, which in turn is/are introduced into a host cell so as to permit recombinant production of TTN and/or analogs thereo. Methods of cloning and expressing large nucleic acids, such as gene clusters, in cells such as *Streptomyces* are well known to those of skill in the art (Stutzman-Engwall and Hutchinson, 1989; Motamedi and Hutchinson, 1987; Grim et al., 1994; Kao et al., 1994; and Hopwood et al., 1987). In some examples, nucleic acid sequences of well over 100 kb have been introduced into cells, including prokaryotic cells, using vector-based methods (see, for example, Osoegawa et al., 1998; Woon et al., 1998; Huang et al., 1996).

A wide variety of expression vectors and host cells are suitable for the synthesis of TTN or analogs thereof. The choice of vector depends on the sequence(s) that are to be expressed. Any transducible cloning vector can be used as a cloning vector for the nucleic acid constructs of this invention. However, where large clusters are to be expressed, phagemids, cosmids, P1s, YACs, BACs, PACs, HACs or similar cloning vectors can be used for cloning the nucleotide sequences into the host cell. Phagemids, cosmids, and BACs, for example, are advantageous vectors due to the ability to insert and stably propagate therein larger fragments of DNA than in M13 phage and lambda phage, respectively. Phagemids which will find use in this method generally include hybrids between plasmids and filamentous phage cloning vehicles. Cosmids which will find use in this method generally include lambda phage-based vectors into which cos sites have been inserted. Recipient pool cloning vectors can be any suitable plasmid. The cloning vectors into which pools of mutants are inserted may be identical or may be constructed to harbor and express different genetic markers (see, e.g., Sambrook et al., 1989). The utility of employing such vectors having different marker genes may be exploited to facilitate a determination of successful transduction. In a certain embodiment, *Streptomyces* vectors are used that include sequences that allow their introduction and maintenance in *E. coli*. Such *Streptomyces/E. coli* shuttle vectors have been described (see, for example, Vara et al., 1989; Guilfoile & Hutchinson, 1991).

The gene sequences, or fragments thereof, which collectively encode the TTN gene cluster, one or more ORFs, can be inserted into expression vectors, using methods known to those of skill in the art, exemplary methods are described in publications written by Cheng et al., 2002; Tang et al., 2004; and Cheng et al., 2003, which are incorporated herein by reference. Suitable expression systems for use with the present invention include systems that function in eukaryotic and prokaryotic host cells. However, as explained above, prokaryotic systems are preferred, and in particular, systems compatible with *Streptomyces* spp. are of particular interest. Control elements for use in such systems include promoters, optionally containing operator sequences, and ribosome binding sites. Exemplary promoters include, but are not limited to bacterial promoters, such as those derived from sugar metabolizing enzymes, such as galactose, lactose (lac) and maltose. Additional examples include promoter sequences derived from biosynthetic enzymes such as tryptophan (trp), the β-lactamase (bla) promoter system, bacteriophage lambda PL, and T5. In addition, synthetic promoters, such as the tac promoter (U.S. Pat. No. 4,551,433, which is incorporated herein by reference in its entirety), which do not occur in nature also function in bacterial host cells. In *Streptomyces*, numerous promoters have been described including constitutive promoters, such as ermE and tcmG (Shen and Hutchinson, 1994), as well as controllable promoters such as actI and actIII (Pleper et al., 1995; Pieper et al., 1995; and Wiesmann et al., 1995).

Other regulatory sequences may also be desirable which allow for regulation of expression of the replacement sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, fore example, enhancer sequences.

Selectable markers can also be included in the recombinant expression vectors. A variety of markers are know which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid. Alternatively, several polyketides are naturally colored and this characteristic provides a built-in marker for selecting cells successfully transformed by the present constructs.

Host cells for the recombinant production of TTN and its analogs can be derived from any organism with the capability of harboring a recombinant 1 nm gene cluster. Thus, the host cells of the present invention can be derived from either prokaryotic or eukaryotic organisms. Particular host cells are those constructed from the actinomycetes, a class of mycelial bacteria that are abundant producers of a number of polyketides and peptides. A particularly useful genus for use with the present system is *Streptomyces*. Thus, for example, *S. verticillus S. ambofaciens, S. avermitilis, S. atroolivaceus, S. azureus, S. cinnamonensis, S. coelicolor, S. curacoi, S. erythraeus, S. fradiae, S. galilaeus, S. glaucescens, S. hygroscopicus, S. lividans, S. parvulus, S. peucetius, S. rimosus, S. roseofulvus, S. thermotolerans, S. violaceoruber*, among others, will provide convenient host cells for the subject invention (see, e.g., Hopwood and Sherman, 1990; O'Hagan, 1991), for a description of various polyketide-producing organisms and their natural products).

Other efficient systems for gene expression in either *E. coli* or *Streptomyces* species can be used in the present invention. For example, the pET (Novagen, Inc., "pET system Mannual" 5$^{th}$ Ed., 1995, Madison, Wis.) or pQE (QIAGEN, Inc. "The QIAexpressionist" 3$^{rd}$ ED., 1997, Santa Clarita, Calif.). The expression efficiency in *E. coli* for genes from *Streptomyces* can be optimized by specific modification at the third positions of the first a few codons of the target gene, taking into account the biased codon usage of streptomycetes (Gramajo et al., 1991). The solubility of the overproduced proteins can be dramatically improved by either co-expression of chaperonins, such as *E. coli* GroEL/S (Wang et al., 2002) or the combination of low incubation temperature (as low as 17° C.), long incubation time (up to 12 hrs after induction), and low or none IPTG induction. The target gene can be expressed either as the native protein or N- or C-terminal fusion proteins. Various pET or pQE vectors for the latter are available that contain different sequences adjacent to the cloning sites. These sequences encode for a variety of peptide "tags" for detection and purification of the target protein. The peptide tags can facilitate isolation of enzymes if difficulty is encountered in the purification of the native proteins. These tags normally do not interfere with the enzyme activities and can be removed if they do become a problem.

D. Mutagenesis

Where employed, mutagenesis can be accomplished by a variety of standard, mutagenic procedures. Mutation is the process whereby changes occur in the quantity or structure of an organism. Mutation can involve modification of the nucleotide sequence of a single gene, blocks of genes or whole chromosomes. Changes in single genes may be the consequence of point mutations which involve the removal, addition or substitution of a single nucleotide base within a DNA sequence, or they may be the consequence of changes involving the insertion or deletion of large numbers of nucleotides. The inventors contemplate introduction of mutations into the pathway to provide mutants that produce various biosynthetic intermediates. Isolation of such intermediates may then allow for semi-synthetic modifications to provide new PTM-like agents. One can also envision that feeding such intermediates to other biosynthetic machineries (possibly in organisms other than *S. platensis*) may provide new "hybrid" natural products.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

i. Random Mutagenesis

Insertional mutagenesis. Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al. 1991). Insertion mutagenesis has been very successful in bacteria and *Drosophila* (Cooley et al. 1988).

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant; in other cases it may vary with each transposition event. Most transposable elements have inverted repeat sequences at their termini. These terminal inverted repeats may be anything from a few bases to a few hundred bases long and in many cases they are known to be necessary for transposition.

Prokaryotic transposable elements have been most studied in *E. coli* and Gram-negative bacteria, but also are present in Gram-positive bacteria. They are generally termed insertion sequences if they are less than about 2 kB long, or transposons if they are longer. Bacteriophages such as mu and D108, which replicate by transposition, make up a third type of transposable element. elements of each type encode at least one polypeptide a transposase, required for their own transposition. Transposons often further include genes coding for function unrelated to transposition, for example, antibiotic resistance genes.

Transposons can be divided into two classes according to their structure. First, compound or composite transposons have copies of an insertion sequence element at each end, usually in an inverted orientation. These transposons require transposases encoded by one of their terminal IS elements. The second class of transposon have terminal repeats of about 30 base pairs and do not contain sequences from IS elements.

Transposition usually is either conservative or replicative, although in some cases it can be both. In replicative transposition, one copy of the transposing element remains at the donor site, and another is inserted at the target site. In conservative transposition, the transposing element is excised from one site and inserted at another.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

Chemical mutagenesis. Chemical mutagenesis offers certain advantages, such as the ability to find a full range of mutant alleles with degrees of phenotypic severity, and is facile and inexpensive to perform. The majority of chemical carcinogens produce mutations in DNA. Benzo[α]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

Radiation mutagenesis. The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2-9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

In Vitro Scanning Mutagenesis. Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

Random mutagenesis by fragmentation and reassmbly. A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

ii. Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants or inactivated mutants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996; Zeng et al., 1996; Burton and Barbas, 1994; Yelton et al., 1995; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

E. Screening

When creating new analogs using the method discussed above, it will be necessary to screen such mutants for desirable activity. By assessing both structural compatability and functional interference with the SHP2 target, it is possible to identify improved inhibitory analogs.

In one embodiment, the analogs can be screened for inhibitory activity against SHP2. Exemplary methods are described in the examples and include a PTP activity assay using pNPP as a substrate. Test compounds are diluted and combined with pNPP, and the reaction is initiated by the addition of concentrated enzyme; pNPP is allowed to convert to the product p-nitrophenol. The reaction can be quenched by the addition of 5N NaOH, and production of p-nitrophenol can be monitored by a spectrophotometer. SHP2-catalyzed hydrolysis of pNPP in the presence of potential inhibitors also facilitates determining mode of inhibition and K, value, discussed further in the examples. Another approach to developing and selecting analogs involves co-crystallization of analogs with SHP2, for example, by hanging drop vapor diffusion methods. The structure may then be solved by molecular replacement using the program AMoRe (Navaza, 1994) and CNS1.1 Brünger et al., 1998). The progress of the refinement can be evaluated by the improvement in the quality of the electron density maps, and the reduced values of the conventional R factor ($R=\Sigma_h||F_o|-|F_c||\Sigma_h|F_o|$), and the free R factor (3.8% of the reflections omitted from the refinement) (Brünger, 1992). Electron density maps can be inspected and the model modified on an interactive graphics workstation with the program O (Jones et al., 1991). Water molecules can be added gradually as a further refinement, assigned in $F_o-F_c$ difference Fourier maps with a 3σ cutoff level for inclusion in the model. The geometry of the final model can be examined with the program PROCHECK (Laskowski et al., 1993).

F. Purification of TTN and Analogs Thereof

Any of a wide variety of chromatographic procedures may be employed to purify the compounds according to the present invention. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

Other methods, including crystallization, distillation, and combinations of these with chromatography can be utilized as well.

An exemplary procedure for extraction and isolation of TTN and analogues from S griseochromo genes wild-type and recombinant strain fermentation is as follows. The fermentation broth (10 L) was harvested by first bringing the broth pH to 4.0 via dropwise addition of 1 N HCl. Fermentation mixtures were then centrifuged at 3800 rpm (SLC-6000 rotor, Sorvall Evolution RC, Thermo Scientific Inc., Waltham, Mass.) at 4° C. for 20 min to pellet the mycelia. Broth supernatants were then collected and filtered to afford transparent amber-colored supernatants. Supernatants were then adsorbed onto 1.8 L of XAD-16 resin twice. Resins (now bearing secondary metabolites) were then washed with 5.4 L of distilled water to remove residual cells and broth components and then subjected to 3.6 L of acetone to elute the absorbed compounds. Acetone was removed under vacuum to give the crude products, and these products were then dissolved into 600 mL of acidic water (pH 4.0). Acidic aqueous fractions were then extracted three times with 900 mL of ethyl acetate (300 mL of fresh solvent each time). The resulting organic layers were combined and dried over anhydrous sodium sulfate. Following removal of all solids, the ethyl acetate was removed under reduced pressure to afford the crude syrups containing TTN and analogues. The syrups were then subjected to column chromatography over silica gel 60 RP-18, eluted with acetonitrile and water (from 2:8 to 9:1; 300 mL each) gradient. Each 100 mL fraction was analyzed by analytical HPLC, employing a detection wavelength of 264 nm and a linear gradient running from a buffer A/buffer B composition of 70:30 to 100% buffer B over the course of 24 min and continued at 100% buffer B for an additional 3 min, at a flow rate of 1 mL/min. Fractions containing TTN or analogues were combined and the solvents removed under reduced pressure for further purification by HPLC on an analytic or semi-preparative C-18 column. Precise purification procedures for each compound are noted below. Following collection of relevant fractions from HPLC, samples were frozen in dry ice and then solvent lyophilized for 12 h.

For purification of TTN, semi-preparative HPLC was carried out on an Alltech Alltima C-18 column (250×10.0 mm, 5 µm), employing a linear gradient from buffer A/buffer B (70:30) to 100% buffer B over 24 min and continued at 100% buffer B for an additional 3 min, at a flow rate of 3 mL/min and monitored by UV detection at 264 nm.

For purification of TTN D-1, the linear gradient went from buffer A/buffer B (90:10) to 100% buffer B over 20 min and continued at 100% buffer B for an additional 3 min, at a flow rate of 3 mL/min and monitored by UV detection at 264 nm.

For purification of diastereomers TTN D-2 and D-3, an effective linear gradient involved ramping from buffer A/buffer B (60:40) to buffer A/buffer B (20:80) over 16 min with continued flow at 100% buffer detection at 264 nm. The first peak corresponded to TTN Dp2, and the slightly slower-moving peak corresponded to TTN D-3. For purification of TTN D-4, the linear gradient went from buffer A/buffer B (70:30) to 100% buffer B over 16 min and continued at 100% buffer B for an additional 2 min, at a flow rate of 3 mL/min and monitored by UV detection at 264 nm.

III. Methods of Treatment

In a particular aspect, the present invention provides methods for the treatment of diseases that involve SHP2 defects, such as inflammation, cancers, autoimmune diseases, Noonan Syndrome and Leopard Syndrome. Treatment methods will involve admininstering to an individual having such a disease an effective amount of a composition containing TTN or an analog thereof. An effective amount is described, generally, as that amount sufficient to detectably and repeatedly to ameliorate, reduce, minimize or limit the extent of the disease or its symptoms. More specifically, it is envisioned that the treatment with TTN or analogs thereof will kill cancer cells, inhibit their growth, and/or otherwise reverse or reduce the symptoms of the disease, modulate immune responses by altering the function of immune cells, and block the function of aberrant SHP2 in Noonan's syndrome and Leopard syndrome.

As discussed above, the SHP2 is a proto-oncogene. It is encoded by the PTPN11 gene, and is a member of the protein tyrosine phosphatase (PTP) family. PTPs are known to be signaling molecules that regulate a variety of cellular processes including cell growth, differentiation, mitotic cycle, and oncogenic transformation. SHP2 contains two tandem Src homology-2 domains, which function as phospho-tyrosine binding domains and mediate the interaction with its substrates. It is widely expressed in most tissues and plays a regulatory role in various cell signaling events that are important for a diversity of cell functions, such as mitogenic activation, metabolic control, transcription regulation, and cell migration.

SHP2, along with its paralogue SHPp1, possesses a domain structure that consists of two tandem SH2 domains in its N-terminus followed by a protein tyrosine phosphatase PTP domain. In the inactive state, the N-terminal SH2 domain binds the PTP domain and blocks access of potential substrates to the active site. Thus, SHP2 is auto-inhibited. Upon binding to target phospho-tyrosyl residues, the N-terminal SH2 domain is released from the PTP domain, catalytically activating the enzyme by releaving this auto-inhibition.

Missense mutations in the PTPN11 locus are associated with both Noonan Syndrome and Leopard Syndrome. In the case of Noonan syndrome, mutations are broadly distributed throughout the coding region of the gene but all appear to result in hyper-activated, or unregulated mutant forms of the protein. Most of these mutations disrupt the binding interface between the N—SH2 domain and catalytic core necessary for the enzyme to maintain its auto-inhibited conformation. The mutations that cause Leopard syndrome are restricted regions affecting the catalytic core of the enzyme producing catalytically impaired SHP2 variants. It is currently unclear how mutations that give rise to mutant variants of SHP2 with biochemically opposite characteristics result in similar human genetic syndromes.

Patients with a subset of Noonan syndrome PTPN11 mutations also have a higher prevalence of juvenile myelomonocytic leukemias. Activating SHP2 mutations have also been detected in neuroblastoma, melanoma, acute myeloid leukemia, breast cancer, lung cancer, colorectal cancer.

A. SHP2-Related Cancers

Cancers that may be treated according to the present invention include cancers of the brain (glioblastomas, medulloblastoma, astrocytoma, oligodendroglioma, ependymomas), lung, liver, spleen, kidney, pancreas, small intestine, blood cells, lymph node, colon, breast, endometrium, stomach, prostate, testicle, ovary, skin, head and neck, esophagus, bone marrow, blood or other tissue. In particular, the present invention relates to the treatment of acute myeloid leukemia, neuroblastoma, melanoma, breast cancer, lung cancer, colorectal cancer.

B. Autoimmune Disease and Other Inflammatory Conditions

1. Autoimmune Disease

An autoimmune disorder that may be treated with TTN or an analog thereof may include, but are not limited to, diabetes melitus, transplantation rejection, multiple sclerosis, premature ovarian failure, scleroderma, Sjogren's disease, systemic lupus erythematosus, vilelego, alopecia (baldness), polyglandular failure, Grave's disease, hypothyroidism, polymyositis, pemphigus, Crohn's disease, colititis, autoimmune hepatitis, hypopituitarism, myocardititis, Addison's disease, autoimmune skin diseases, uveititis, pernicious anemia, hypoparathyroidism, and/or rheumatoid arthritis.

2. Sepsis

Sepsis is a serious medical condition characterized by a whole-body inflammatory state caused by infection. Traditionally the term sepsis has been used interchangeably with septicaemia and septicemia ("blood poisoning"). However, these terms are no longer considered synonymous; septicemia is considered a subset of sepsis.

Symptoms of sepsis are often related to the underlying infectious process. When the infection crosses into sepsis, the resulting symptoms are that of systemic inflammatory response syndrome (SIRS): general inflammation, fever, elevated white blood cell count (leukocytosis), and raised heart rate (tachycardia) and breathing rate (tachypnea). Secondary to the above, symptoms also include flu like chills.

The immunological response that causes sepsis is a systemic inflammatory response causing widespread activation of inflammation and coagulation pathways. This may progress to dysfunction of the circulatory system and, even under optimal treatment, may result in the multiple organ dysfunction syndrome and eventually death.

Sepsis is considered present if infection is highly suspected or proven and two or more of the following systemic inflammatory response syndrome (SIRS) criteria are met:

heart rate >90 beats per minute
body temperature <36 (96.8° F.) or >38° C. (100.4° F.)
hyperventilation (high respiratory rate)>20 breaths per minute or, on blood gas, a $P_aCO_2$ less than 32 mm Hg
white blood cell count <4000 cells/mm$^3$ or >12000 cells/mm$^3$ (<4×10$^9$ or >12×10$^9$ cells/L), or greater than 10% band forms (immature white blood cells).

Consensus definitions however continue to evolve with the latest expanding the list of signs and symptoms of sepsis to reflect clinical bedside experience.

The more critical subsets of sepsis are severe sepsis (sepsis with acute organ dysfunction) and septic shock (sepsis with refractory arterial hypotension). Alternatively, when two or more of the systemic inflammatory response syndrome criteria are met without evidence of infection, patients may be diagnosed simply with "SIRS." Patients with SIRS and acute organ dysfunction may be termed "severe SIRS."

Patients are defined as having "severe sepsis" if they have sepsis plus signs of systemic hypoperfusion; either end organ dysfunction or a serum lactate greater than 4 mmol/dL. Patient are defined as having septic shock if they have sepsis plus hypotension after an appropriate fluid bolus (typically 20 ml/kg of crystaloid). The criteria for diagnosing an adult with sepsis do not apply to infants under one month of age. In infants, only the presence of infection plus a "constellation" of signs and symptoms consistent with the systemic response to infection are required for diagnosis.

The therapy of sepsis rests on antibiotics, surgical drainage of infected fluid collections, fluid replacement and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition, if necessary by parenteral nutrition, is important during prolonged illness.

A problem in the adequate management of septic patients has been the delay in administering therapy after sepsis has been recognized. Published studies have demonstrated that for every hour delay in the administration of appropriate antibiotic therapy there is an associated 7% rise in mortality. A large international collaboration was established to educate people about sepsis and to improve patient outcomes with sepsis, entitled the "Surviving Sepsis Campaign." The Campaign has published an evidence-based review of management strategies for severe sepsis, with the aim to publish a complete set of guidelines in subsequent years.

Most therapies aimed at the inflammatory process itself have failed to improve outcome, however drotrecogin alfa (activated protein C, one of the coagulation factors) has been shown to decrease mortality from about 31% to about 25% in severe sepsis. To qualify for drotrecogin alfa, a patient must have severe sepsis or septic shock with an APACHE II score of 25 or greater and a low risk of bleeding. Low dose hydrocortisone treatment has shown promise for septic shock patients with relative adrenal insufficiency as defined by ACTH stimulation testing.

Standard treatment of infants with suspected sepsis consists of supportive care, maintaining fluid status with intravenous fluids, and the combination of a β-lactam antibiotic (such as ampicillin) with an aminoglycoside such as gentamicin.

3. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pre-treatment (in the case of a medical procedure) and treatment after trauma injury as occurred.

Surgery. Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called noninvasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty. By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

Traumatic Hemorrhage. Traumatic hemorrhage accounts for much of the wide ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provide. Finally, the critical care phase provides for post-operative support and tissue perfusion.

4. Acute Pancreatitis

Acute pancreatitis is rapidly-onset inflammation of the pancreas. Depending on its severity, it can have severe complications and high mortality despite treatment. While mild cases are often successfully treated with conservative measures or laparoscopy, severe cases require invasive surgery (often more than one intervention) to contain the disease process.

5. Acute Respiratory Distress Syndrome

Acute respiratory distress syndrome (ARDS), also known as respiratory distress syndrome (RDS) or adult respiratory distress syndrome (in contrast with IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators causing inflammation, hypoxemia and frequently resulting in multiple organ failure. This condition is life threatening and often lethal, usually requiring mechanical ventilation and admission to an intensive care unit. A less severe form is called acute lung injury (ALI). ARDS can occur within 24 to 48 hours of an injury or attack of acute illness. In such a case the patient usually presents with shortness of breath, tachypnea, and symptoms related to the underlying cause, i.e., shock. Long term illnesses can also trigger it, such as malaria. The ARDS may then occur sometime after the onset of a particularly acute case of the infection.

An arterial blood gas analysis and chest X-ray allow formal diagnosis by inference using the aforementioned criteria. Although severe hypoxemia is generally included, the appropriate threshold defining abnormal $PaO_2$ has never been systematically studied. Any cardiogenic cause of pulmonary edema should be excluded. This can be done by placing a pulmonary artery catheter for measuring the pulmonary artery wedge pressure. However, this is not necessary and is now rarely done as abundant evidence has emerged demonstrating that the use of pulmonary artery catheters does not lead to improved patient outcomes in critical illness including ARDS. Plain chest X-rays are sufficient to document bilateral alveolar infiltrates in the majority of cases. While CT scanning leads to more accurate images of the pulmonary parenchyma in ARDS, its has little utility in the clinical management of patients with ARDS, and remains largely a research tool.

Acute respiratory distress syndrome is usually treated with mechanical ventilation in the Intensive Care Unit. Ventilation is usually delivered through oro-tracheal intubation, or tracheostomy whenever prolonged ventilation ($\geq 2$ weeks) is deemed inevitable. The possibilities of non-invasive ventilation are limited to the very early period of the disease or, better, to prevention in individuals at risk for the development of the disease (atypical pneumonias, pulmonary contusion, major surgery patients). Treatment of the underlying cause is imperative, as it tends to maintain the ARDS picture. Appropriate antibiotic therapy must be administered as soon as microbiological culture results are available. Empirical therapy may be appropriate if local microbiological surveillance is efficient. More than 60% ARDS patients experience a (nosocomial) pulmonary infection either before or after the onset of lung injury. The origin of infection, when surgically treatable, must be operated on. When sepsis is diagnosed, appropriate local protocols should be enacted.

6. Ischemia-Reperfusion Injury

Reperfusion injury refers to damage to tissue caused when blood supply returns to the tissue after a period of ischemia. The absence of oxygen and nutrients from blood creates a condition in which the restoration of circulation results in inflammation and oxidative damage through the induction of oxidative stress rather than restoration of normal function.

The damage of reperfusion injury is due in part to the inflammatory response of damaged tissues. White blood cells carried to the area by the newly returning blood release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Repeated bouts of ischemia and reperfusion injury also are thought to be a factor leading to the formation and failure to heal of chronic wounds such as pressure sores and diabetic foot ulcers. Continuous pressure limits blood supply and causes ischemia, and the inflammation occurs during reperfusion. As this process is repeated, it eventually damages tissue enough to cause a wound.

In prolonged ischemia (60 min or more), hypoxanthine is formed as breakdown product of ATP metabolism. The enzyme xanthine dehydrogenase is converted to xanthine oxidase as a result of the higher availability of oxygen. This oxidation results in molecular oxygen being converted into highly reactive superoxide and hydroxyl radicals. Xanthine oxidase also produces uric acid, which may act as both a prooxidant and as a scavenger of reactive species such as peroxinitrite. Excessive nitric oxide produced during reperfusion reacts with superoxide to produce the potent reactive species peroxynitrite. Such radicals and reactive oxygen species attack cell membrane lipids, proteins, and glycosaminoglycans, causing further damage. They may also initiate specific biological processes by redox signaling.

7. Cardiovascular Disease

Cardiovascular disease refers to the class of diseases that involve the heart or blood vessels (arteries and veins). While the term technically refers to any disease that affects the cardiovascular system, it is usually used to refer to those related to atherosclerosis (arterial disease). These conditions have similar causes, mechanisms, and treatments. Treatment of cardiovascular disease depends on the specific form of the disease in each patient, but effective treatment always includes preventive lifestyle changes discussed above. Medications, such as blood pressure reducing medications, aspirin and the statin cholesterol-lowering drugs may be helpful. In some circumstances, surgery or angioplasty may be warranted to reopen, repair, or replace damaged blood vessels Most Western countries face high and increasing rates of cardiovascular disease. Each year, heart disease kills more Americans than cancer. Diseases of the heart alone caused 30% of all deaths, with other diseases of the cardiovascular system causing substantial further death and disability. Up until the year 2005, it was the number 1 cause of death and disability in the United States and most European countries. A large histological study (PDAY) showed vascular injury accumulates from adolescence, making primary prevention efforts necessary from childhood.

Some biomarkers are thought to offer a more detailed risk of cardiovascular disease. However, the clinical value of these biomarkers is questionable. Currently, biomarkers which may reflect a higher risk of cardiovascular disease include:
  higher fibrinogen and PAI-1 blood concentrations
  hlevated homocysteine, or even upper half of normal
  elevated blood levels of asymmetric dimethylarginine
  high inflammation as measured by C-reactive protein
  levated blood levels of B-type natriuretic peptide (BNP)

Various forms of cardiovascular disease include aneurysms, angina, arrhythmia, atherosclerosis, cardiomyopathy, cerebrovascular disease, congenital heart disease, congestive heart failure, myocarditis, valve disease, coronary artery disease, dilated cardiomyopathy, diastolic dysfunction, endocarditis, high blood pressure (hypertension), hypertrophic cardiomyopathy, nitral valve prolapse, myocardial infarction, and venous thromboembolism.

8. Chemotherapy, Radiotherapy and Cytokine Therapy Toxicity

Various forms of cancer therapy, including chemotherapy, radiation, and cytokines, are associated with toxicity, sometimes severe, in the cancer patient. To the extent that the toxicity is caused at least in part by the extracellular actions of histones, the present invention seeks to reduce this toxicity using the pharmaceutical compositions of the present invention, thereby reducing or alleviating discomfort on the part of the patient, as well as permitting higher doses of the therapy.

9. Burns

In medicine, a burn may be an injury caused by heat, cold, electricity, chemicals, friction or radiation. First-degree burns are usually limited to redness (erythema), a white plaque, and minor pain at the site of injury. These burns usually extend only into the epidermis. Second-degree burns additionally fill with clear fluid, have superficial blistering of the skin, and can involve more or less pain depending on the level of nerve involvement. Second-degree burns involve the superficial (papillary) dermis and may also involve the deep (reticular) dermis layer. Third-degree burns additionally have charring of the skin, and produce hard, leather-like eschars. An eschar is a scab that has separated from the unaffected part of the body. Frequently, there is also purple fluid. These types of burns are often painless, because nerve endings have been destroyed in the burned areas. Serious burns, especially if they cover large areas of the body, can cause death; any hint of burn injury to the lungs (e.g., through smoke inhalation) is a medical emergency.

Burns that injure the tissues underlying the skin, such as the muscles or bones, are sometimes categorized as fourth-degree burns. These burns are broken down into three additional degrees: fourth-degree burns result in the skin being irretrievably lost, fifth-degree burns result in muscle being irretrievably lost, and sixth-degree burns result in bone being charred.

A newer classification of "Superficial Thickness," "Partial Thickness" (which is divided into superficial and deep categories) and "Full Thickness" relates more precisely to the epidermis, dermis and subcutaneous layers of skin and is used to guide treatment and predict outcome.

Chemical burns are usually caused by chemical compounds, such as sodium hydroxide (lye), silver nitrate, and more serious compounds (such as sulfuric acid). Most chemicals (but not all) that can cause moderate to severe chemical burns are strong acids or bases. Nitric acid, as an oxidizer, is possibly one of the worst burn-causing chemicals. Hydrofluoric acid can eat down to the bone and its burns are often not immediately evident. Most chemicals that can cause moderate to severe chemical burns are called caustic.

Electrical burns are generally symptoms of electric shock, being struck by lightning, being defibrillated or cardioverted without conductive gel, etc. The internal injuries sustained may be disproportionate to the size of the "burns" seen—as these are only the entry and exit wounds of the electrical current.

Burns are assessed in terms of total body surface area (TBSA), which is the percentage affected by partial thickness or full thickness burns (superficial thickness burns are not counted). The rule of nines is used as a quick and useful way to estimate the affected TBSA. The first step in managing a person with a burn is to stop the burning process. With dry powder burns, the powder should be brushed off first. With other burns, the affected area should be rinsed with a large amount of clean water to remove foreign bodies and help stop the burning process. Cold water should never be applied to any person with extensive burns, as it may severely compromise the burn victim's temperature status. At this stage of management, it is also critical to assess the airway status. If the patient was involved in a fire, then it must be assumed that he or she has sustained inhalation injury until proven otherwise, and treatment should be managed accordingly.

Once the burning process has been stopped, and airway status is ensured, the patient should be volume resuscitated according to the Parkland formula. This formula dictates that the amount of Lactated Ringer's solution to deliver in the first twenty four hours after time of injury is:

fluid=4 cc x % TBSA x weight in kg

% TBSA excludes any first degree burn
Half of this fluid should be given in the first eight hours post injury and the rest in the subsequent sixteen hours. The formula is a guide only and infusions must be tailored to urine output and central venous pressure. Inadequate fluid resuscitation causes renal failure and death. Severe edema in full thickness burns may be treated by escharotomy.

C. Noonan Syndrome

Noonan Syndrome (NS) is a relatively common autosomal dominant congenital disorder considered to be a type of dwarfism, that affects both males and females equally. It used to be referred to as the male version of Turner's syndrome (and is still sometimes described in this way); however, the genetic causes of Noonan syndrome and Turner syndrome are distinct. The principal features include congenital heart defect, short stature, learning problems, indentation of the chest, impaired blood clotting, and a characteristic configuration of facial features. The syndrome is named after Dr. Jacqueline Noonan.

It is believed that between approximately 1 in 1,000 and 1 in 2,500 children worldwide are born with NS. It is one of the most common genetic syndromes associated with congenital heart disease, similar in frequency to Down syndrome. However, the range and severity of features can vary greatly in patients with NS. Therefore, the syndrome is not always identified at an early age.

Recurrence in siblings and apparent transmission from parent to child has long suggested a genetic defect with autosomal dominant inheritance and variable expression. A person with NS has up to a 50% chance of transmitting it to a child. The fact that an affected parent is not always identified for children with NS suggests several possibilities: (a) manifestations are variably expressed and could be so subtle as to go unrecognized (variable expressivity); (b) a high proportion of cases represent new, sporadic mutations or (c) Noonan syndrome is heterogeneous, comprising more than one similar condition of differing cause, some not inherited.

Despite identification of four causative genes, the diagnosis of Noonan syndrome is still based on clinical features. In other words, it is made when a physician feels that a patient has enough of the features to warrant the label indicating association. The patient can be tested for mutations in the SHP2, SOS1, or KRAS genes, however absence of a mutation will not exclude the diagnosis as there are more as yet undiscovered genes that cause NS. The principal values of making such a diagnosis are that it guides additional medical and developmental evaluations, it excludes other possible explanations for the features, and it allows more accurate recurrence risk estimates.

D. Leopard Syndrome

LEOPARD syndrome (also known as "cardiocutaneous syndrome," "Gorlin syndrome II," "lentiginosis profusa syndrome," "progressive cardiomyopathic lentiginosis," "Capute-Rimoin-Konigsmark-Esterly-Richardson syndrome" or "Moynahan syndrome") is part of a group called Ras/MAPK pathway syndromes. It is a rare autosomal dominant, multisystem disease caused by a mutation in the SHP2gene (PTPN11). The disease is a complex of features, mostly involving the skin, skeletal and cardiovascular systems, they may or may not be present in all patients. The nature of how the mutation causes each of the condition's symptoms is not well known, however research is ongoing.

Related to Noonan syndrome, LEOPARD syndrome is caused by a different missense mutation of the same gene. Noonan syndrome is fairly common (1:1000 to 1:2500 live births), and neurofibromatosis 1 (which was once thought to be related to LEOPARD syndrome) is also common (1:3500), however no epidemiologic data exists for LEOPARD syndrome. The name of the condition is a mnemonic, originally coined in 1969, as the condition is characterized by seven conditions, the first letters of which spell LEOPARD, including the characteristic "freckling" of the skin, caused by the lentigines that is reminiscent of the large cat.

A clinical diagnosis is considered made when, with lentigines present there are 2 other symptoms observed, such as ECG abnormalities and ocular hypertelorism, or without lentigines, 3 of the above conditions are present, with a first-degree relative (i.e., parent, child, sibling) with a clinical diagnosis. Mild mental retardation is observed in about 30% of those affected with the syndrome Nystagmus (involuntary eye movements), seizures, or hyposmia (reduced ability to smell) has been documented in a few patients. In 2004, a patient was reported with recurrent upper extremity aneurysms that required surgical repairs. In 2006, a LEOPARD syndrome patient was reported with acute myelogenous leukemia.

There are 5 identified allelic variants responsible for LEOPARD syndrome. Y279C, T468M, A461T, G464A, and Q510P which seems to be a unique familial mutation, in that all other variants are caused by transition errors, rather than transversion. In the two predominant mutations of LEOPARD syndrome (Y279C and T468M), the mutations cause a loss of catalytic activity of the SHP2 protein(the gene product of the PTPN11 gene), which is a previously unrecognized behavior for this class of mutations. This interferes with growth factor and related signalling. While further research confirms this mechanism, additional research is needed to determine how this relates to all of the observed effects of LEOPARD syndrome.

It is suggested that, once diagnosed, individuals be routinely followed by a cardiologist, endocrinologist, dermatologist, and other appropriate specialties as symptoms present. It is recommended that those with the syndrome who are capable of having children seek genetic counseling before deciding to have children. As the syndrome presents frequently as a forme fruste (incomplete, or unusual form) variant, an examination of all family members must be undertaken. As an autosomal dominant trait there is a fifty percent chance with each child, that they will also be born with the syndrome. This does not take into account the possibility of the gene mutating, on its own, in a child of a LEOPARD syndrome patient who does not inherit the gene from the affected parent. Although fully penetrant, since the syndrome has variable expressivity, one generation may have a mild expression of the syndrome, while the next may be profoundly affected. Once a decision to have children is made, and the couple conceives, the fetus is monitored during the pregnancy for cardiac evaluation. If a gross cardiac malformation is found, parents receive counseling on continuing with the pregnancy.

For those with endocrine issues (low levels of thyrotopin [a pituitary hormone responsible for regulating thyroid hormones], follicle stimulating hormone) drug therapy is recommended. For those who are disturbed by the appearance of lentigines, cryosurgery may be beneficial. Due to the large number of lentigines this may prove time consuming. An alternative treatment with tretinoin or hydroquinone creams may help. Drug therapies for those with cardiac abnormalities, as those abnormalities become severe enough to warrant the use of these therapies. ECG's are mandatory prior to any surgical interventions, due to possible arrythmia.

E. Dosages

In certain embodiments, the TTN or analog thereof is administered to a subject. An effective amount of TTN or analog that may be administered to a cell includes a dose of about −0.1 µM to about 100 µM. More specifically, doses of TTN or analog to be administered are from about 0.1 µM to about 1 µM; about 1 µM to about 5 µM; about 5 µM to about 10 µM; about 10 µM to about 15 µM; about 15 µM to about 20 µM; about 20 µM to about 30 µM; about 30 µM to about 40 µM; about 40 µM to about 50 µM; about 50 µM to about 60 µM; about 60 µM to about 70 µM; about 70 µM to about 80 µM; about 80 µM to about 90 µM; and about 90 µM to about 100 µM. Of course, all of these amounts are exemplary, and any amount in-between these points is also expected to be of use in the invention.

In another embodiment of the invention, the dose range of the TTN or analogs thereof will be measured by body weight, for example, about 0.5 mg/kg body weight to about 500 mg/kg body weight. Those of skill will recognize the utility of a variety of dosage range, for example, 1 mg/kg body weight to 450 mg/kg body weight, 2 mg/kg body weight to 400 mg/kg body weighty, 3 mg/kg body weight to 350 mg/kg body weighty, 4 mg/kg body weight to 300 mg/kg body weight, 5 mg/kg body weight to 250 mg/kg body weighty, 6 mg/kg body weight to 200 mg/kg body weight, 7 mg/kg body weight to 150 mg/kg body weighty, 8 mg/kg body weight to 100 mg/kg body weight, or 9 mg/kg body weight to 50 mg/kg body weight. Further, those of skill will recognize that a variety of different dosage levels will be of use, for example, 1 mg/kg, 2 mg/kg, 3 mg/kg, 4 mg/kg, 5 mg/kg, 7.5 mg/kg, 10 mg/kg, 12.5 mg/kg, 15 mg/kg, 17.5 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 120 mg/kg, 140 mg/kg, 150 mg/kg, 160 mg/kg, 180 mg/kg, 200 mg/kg, 225 mg/kg, 250 mg/kg, 275 mg/kg, 300 mg/kg, 325 mg/kg, 350 mg/kg, 375 mg/kg, 400 mg/kg, 450 mg/kg, 500 mg/kg, 550 mg/kg, 600 mg/kg, 700 mg/kg, 750 mg/kg, 800 mg/kg, 900 mg/kg, 1000 mg/kg, 1250 mg/kg, 1500 mg/kg, 1750 mg/kg, 2000 mg/kg, 2500 mg/kg, and/or 3000 mg/kg. Of course, all of these dosages are exemplary, and any dosage in-between these points is also expected to be of use in the invention. Any of the above dosage ranges or dosage levels may be employed for TTN or analogs thereof.

The treatments may include various "unit doses." Unit dose is defined as containing a predetermined-quantity of the therapeutic composition (TTN or its analogs) calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time.

As is well known in the art, a specific dose level of active compounds such as TTN or analogs thereof for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

F. Formulations and Routes for Administration

Pharmaceutical compositions of the present invention comprise an effective amount of one or more candidate substance or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one candidate substance or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The candidate substance may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, subcutaneously, subconjunctival, intravesicularlly, mucosally, intrapericardially, intraumbilically, intraocularally, orally, locally, via inhalation (e.g., aerosol inhalation), via injection, via infusion, via continuous infusion, via localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The candidate substance may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the candidate substance is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

G. Combined Therapy

In the context of the present invention, it is contemplated that the TTN or analogs thereof may be used in combination with an additional anti-cancer or immunotherapeutic agent to more effectively treat cancer or auto-immunity.

When an additional therapeutic agent is administered, as long as the dose of the additional therapeutic agent does not exceed previously quoted toxicity levels, the effective amounts of the additional therapeutic agent may simply be defined as that amount effective to exert a therapeutic effect when administered to an animal in combination with the TTN or analog thereof. This may be easily determined by monitoring the animal or patient and measuring those physical and biochemical parameters of health and disease that are indicative of the success of a given treatment. Such methods are routine in animal testing and clinical practice.

To kill or slow the growth of a cancer cell using the methods and compositions of the present invention, or to modulate an immune response, one can provide to the subject a TTN or analog thereof in combination with an additional therapeutic agent. These compositions would be provided in a combined amount effective to effect a therapeutic benefit (inhibition of cancer cell growth, reduction in tumor size, induction of apoptosis in a cancer cell, down-regulating of an autoimmune response, etc.). This process may involve administering TTN or analog thereof in combination with an additional therapeutic agent or factor(s) at the same time. This may be achieved by administering a single composition or pharmacological formulation that includes both agents, or by administering two distinct compositions or formulations, at the same time, wherein one composition includes TTN or analog thereof and the other includes the additional agent.

Alternatively, treatment with TTN or analog thereof may precede or follow the additional agent treatment by intervals ranging from minutes to weeks. In embodiments where the additional agent is administered separately to the patient, one would generally ensure that a significant period of time did not expire between the time of each delivery, such that the agent would still be able to exert an advantageously combined effect on the cell. In such instances, it is contemplated that one would contact the cell with both modalities within about 12-24 hr of each other and, more preferably, within about 6-12 hr of each other, with a delay time of only about 12 hr being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either TTN or analog thereof in combination with an additional therapeutic agent such as anticancer agent or immunosuppressive agent will be desired. Various combinations may be employed, where TTN or analog thereof is "A" and the additional agent is "B," as exemplified below:

| A/B/A | B/A/B | B/B/A | A/A/B | B/A/A | A/B/B | B/B/B/A | B/B/A/B |
|-------|-------|-------|-------|-------|-------|---------|---------|
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Agents or factors suitable for use in a combined cancer therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In treating cancer according to the invention, one would contact a tumor or tumor cells with an agent according to the present invention along with the second agent or therapy. This may be achieved by irradiating the localized tumor site with radiation such as X-rays, UV-light, γ-rays or even microwaves. Alternatively, the tumor or tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a compound according to the present invention.

Agents that directly cross-link nucleic acids, specifically DNA, are envisaged to facilitate DNA damage leading to a synergistic, antineoplastic combination with Killin. Agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

5-FU has been the first-choice chemotherapy drug for colorectal cancer for many years. It is used in combination with leucovorin (a vitamin), which makes 5-FU more effective. Recently, a pill form of 5-FU has been developed, called Xeloda®, which is used for colorectal cancer that has spread to other organs. Xeloda® is also being used as neoadjuvant therapy with radiation in patients with rectal cancers to heighten the effect of radiation.

Several new chemotherapy drugs also are used for the treatment of colorectal cancer that has spread. These include Camptosar®, Eloxatin®, Avastin®, Erbitux®, and Vectibix®. Camptosar®, Eloxatin®, and Avastin® are usually given along with 5-FU for metastatic colorectal cancer. Erbitux® is administred intravenously either alone or with Camptosar®. Vectibix® is usually given in combination with 5-FU and leucovorin.

With respect to autoimmune disorders, second agents include steroids, glucocorticoids, non-steriodal anti-inflammatory drugs (NSAIDS; including COX-1 and COX-2 inhibitors), aspirin, ibuprofen, and naproxen.

The skilled artisan is directed to "Remington's Pharmaceutical Sciences" 15th Edition, chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

H. Assessing SHP2 Mutations

Assessing mutations can be performed using methods as previously described in Small, K. M., et al., *Methods Enzymol*, 343:459-75 (2002), which is incorporated herein by reference. It will be understood by the skilled artisan that other standard techniques are available for genotyping and any technique may be used with the present invention.

Those in the art will readily recognize that nucleic acid molecules may be double-stranded molecules and that reference to a particular site on one strand refers, as well, to the corresponding site on a complementary strand. Thus, in defining a polymorphic site, reference to an adenine, a thymine (uridine), a cytosine, or a guanine at a particular site on the plus (sense or coding) strand of a nucleic acid molecule is also intended to include the thymine (uridine), adenine, guanine, or cytosine (respectively) at the corresponding site on a minus (antisense or noncoding) strand of a complementary strand of a nucleic acid molecule. Thus, reference may be made to either strand and still comprise the same polymorphic site and an oligonucleotide may be designed to hybridize to either strand. Throughout the text, in identifying a polymorphic site, reference is made to the sense strand, only for the purpose of convenience.

Typically, the nucleic acid mixture is isolated from a biological sample taken from the individual, such as a blood sample or tissue sample using standard techniques such as disclosed in Jones, A. S., *Nature*, 199:280-2 (1963) which is hereby incorporated by reference. Suitable tissue samples include whole blood, semen saliva, tears, urine, fecal material, sweat, buccal, skin and hair. The nucleic acid mixture may be comprised of genomic DNA, mRNA, or cDNA and, in the latter two cases, the biological sample must be obtained from an organ in which the $\beta_1$AR gene is expressed. Furthermore it will be understood by the skilled artisan that mRNA or cDNA preparations would not be used to detect mutations located in introns or in 5' and 3' nontranscribed regions.

Target region(s) may be amplified using any oligonucleotide-directed amplification method, including but not limited to polymerase chain reaction (PCR) (U.S. Pat. No. 4,965, 188), ligase chain reaction (LCR) (Barany, et al., *Proc. Natl. Acad. Sci. USA*, 88:189-193, 1991; WO90/01069), and oligonucleotide ligation assay (OLA) (Landegren, et al., *Science*, 241:1077-1080 (1988)). Oligonucleotides useful as primers or probes in such methods should specifically hybridize to a region of the nucleic acid that contains or is adjacent to the polymorphic site. Typically, the oligonucleotides are between 10 and 35 nucleotides in length and preferably, between 15 and 30 nucleotides in length. Most preferably, the oligonucleotides are 20 to 25 nucleotides long. The exact length of the oligonucleotide will depend on many factors that are routinely considered and practiced by the skilled artisan. Other known nucleic acid amplification procedures may be used to amplify the target region including transcription-based amplification systems (U.S. Pat. No. 5,130,238; EP 329,822; U.S. Pat. No. 5,169,766, WO89/06700) and isothermal methods (Walker, et al., *Proc. Natl. Acad. Sci. USA,* 89:392-396 (1992).

A mutation in the target region may also be assayed before or after amplification using one of several hybridization-based methods known in the art. Typically, mutation-specific oligonucleotides are utilized in performing such methods. The mutation-specific oligonucleotides may be used as differently labeled probe pairs, with one member of the pair showing a perfect match to one variant of a target sequence and the other member showing a perfect match to a different variant. In some embodiments, more than one mutation site may be detected at once using a set of mutation-specific oligonucleotides or oligonucleotide pairs.

Hybridization of an mutation-specific oligonucleotide to a target polynucleotide may be performed with both entities in solution, or such hybridization may be performed when either the oligonucleotide or the target polynucleotide is covalently or noncovalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Mutation-specific oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the mutation-specific oligonucleotide or target nucleic acid.

The identity of mutations may also be determined using a mismatch detection technique, including but not limited to the RNase protection method using riboprobes (Winter, et al., *Proc. Natl. Acad. Sci. USA,* 82:7575 (1985); Meyers, et al., *Science,* 230:1242 (1985) and proteins which recognize nucleotide mismatches, such as the *E. coli* mutS protein (Modrich, P., *Ann. Rev. Genet.,* 25:229-253 (1991). Alternatively, mutations can be identified by single-strand conformation polymorphism (SSCP) analysis (Orita et al., *Genomics,* 5:874-879 (1989); Humphries, et al., in Molecular Diagnosis of Genetic Diseases, R. Elles, ed., pp 321-340, 1996) or denaturing gradient gel electrophoresis (DGGE) (Wartell, et al., *Nucl. Acids Res.,* 18:2699-2706 (1990); Sheffield, et al., *Proc. Natl. Acad. Sci. USA,* 86:232-236, 1989).

A polymerase-mediated primer extension method may also be used to identify the polymorphism(s). Several such methods have been described in the patent and scientific literature. Extended primers containing a polymorphism may be detected by mass spectrometry as described in U.S. Pat. No. 5,605,798. An other primer extension method is allele-specific PCR (Ruano, et al., *Nucl. Acids Res.,* 17:8392 (1989); Ruano, et al., *Nucl. Acids Res.,* 19:6877-6882 (1991); WO 93/22456; Turki, et al., *J. Clin. Invest.,* 95: 1635-1641 (1995).

1. Hybridization

The use of a probe or primer of between 7, 8, 9, 10, 11, 12, 13, 14, 15, 16, 17, 18, 19, 20, 21, 22, 23, 24, 25, 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M $NaHPO_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCRTM (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

The most commonly used method of characterizing a mutation is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'-to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

French Patent 2,650,840 and PCT Application WO91/02087 discuss a solution-based method for determining the identity of the nucleotide of a polymorphic site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected.

IV. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Materials. TTM, TTN, and the engineered analogs are produced as described previously (Li et al., 2008; Ju et al., 2009; Li et al., 2009; Luo et al., 2010). Polyethylene glycol (PEG3350) and buffers for crystallization were purchased from Hampton Research Co. p-Nitrophenyl phosphate (pNPP) was purchased from Fluke Co. Dithiothreitol (DTT) was provided by Fisher (Fair Lawn, N.J.). All of other chemicals and reagents were of the highest commercially available grade. The expression and purification of the SHP2 catalytic domain (residues 262-528) were described previously (Zhang et al., 2010).

Kinetic Analysis of SHP2 Inhibition by TTM, TTN and Analogs.

The PTP activity was assayed using pNPP as a substrate at 25° C. in 50 mM 3,3-dimethylglutarate buffer, pH 7.0, containing 1 mM EDTA with an ionic strength of 0.15 M adjusted by NaCl. TTM, TTN and the engineered analogs were analyzed for inhibition of a panel of PTPs at 10 µM compound concentration. For each enzyme screened, test compounds were diluted to 20 µM in 100 µL and combined with 50 µL pNPP at a concentration of 4×$K_m$. The reaction was initiated by the addition of 50 µL of 4× concentrated enzyme and pNPP was allowed to convert to the product p-nitrophenol. The reaction was quenched by the addition of 50 µL of 5N NaOH. Nonenzymatic hydrolysis of pNPP was corrected by measuring the control without the addition of enzyme. Production of p-nitrophenol was monitored by a Spectra MAX385 microplate spectrophotometer (Molecular Devices) at 405 nm using a molar extinction coefficient of 18,000 $M^{-1}$ $cm^{-1}$. $IC_{50}$ values were calculated by fitting the absorbance at 405 nm versus inhibitor concentration to the following equation:

$$A_I/A_0 = IC_{50}/(IC_{50}+[I])$$

where $A_I$ is the absorbance at 405 nm of the sample in the presence of inhibitor; $A_o$ is the absorbance at 405 nm in the absence of inhibitor; and [I] is the concentration of the inhibitor.

$K_i$ Measurement.

The SHP2-catalyzed hydrolysis of pNPP in the presence of TTN or TTN D-1 was assayed at 25° C. and in the assay buffer described above. The mode of inhibition and $K_i$ value were determined in the following manner. At various fixed concentrations of the inhibitor (0-3 $K_i$), the initial rate at a series of pNPP concentrations was measured by following the production of p-nitrophenol as describe above, ranging from 0.2- to 5-fold the apparent $K_m$ values. The data were fitted to appropriate equations using SigmaPlot-Enzyme Kinetics to obtain the inhibition constant and to assess the mode of inhibition.

Cell Culture and Immunoblotting.

Jurkat T cells were grown at 37° C. under an atmosphere of 5% $CO_2$ in RPMI medium 1640 supplemented with 10% FBS. Cells were pretreated with different concentrations of TTN, TTN D-1, or TTM for 2 hours and stimulated with 10 mg/mL anti-CD3 antibody (OKT3; eBioscience) for 5 min and 30 min, respectively. Subsequently, cells were spinned down at 2000 rpm in 4° C., and cell pellets were lysed in 50 mM Tris-HCl (pH 7.5), 150 mM NaCl, 10% glycerol, 1% NP-40, 50 mM NaF, 10 mM pyrophosphate, 5 mM idoacetate, 1 mM sodium orthovanadate, and the protease inhibitor mixture. After 30 min lysing on ice, the cell lysates were centrifuged at 13,200 rpm for 15 min. Total cellular proteins were separated by SDS/PAGE and transferred electrophoretically to nitrocellulose membrane, which was immunoblotted by appropriate antibodies followed by incubation with HRP-conjugated secondary antibodies. Blots were developed using Pierce Pico ECL reagent (Thermo) according to the manufacturer's instructions.

Biochemical Analysis.

Bone marrow low density mononuclear cells (LDMNCs) were transduced with MIEG3 (empty vector), MIEG3-WT SHP2, or MIEG3-SHP2/E76K, sorted based on enhanced green fluorescent protein (EGFP) expression, and cultured for 5 days in M-CSF 100 ng/mL to generate macrophage progenitors, as previously described (Chan et al., 2005). Cells were serum- and growth factor-deprived for 16 hours, treated with 2 µM TTN for 2 hours, and stimulated with GM-CSF 50 ng/mL followed by preparation of protein extracts. Extracts were evaluated by immunoblot using α-phospho-ERK1/2 for activated ERK levels and α-ERK1/2 for total ERK levels (Cell Signaling Technology, Beverly, Mass.).

Hematopoietic Progenitor Analysis.

Transduced, EGFP+ cells were subjected to $^3$H-thymidine incorporation assays, as previously described (Munugalavadla et al., 2007), or plated at a concentration of 8000 cells/mL in 0.9% methylcellulose-based media containing IMDM, 2 mM glutamine, 1% penicillin/streptomycin, 80 µM β-mercaptoethanol, 30% FBS, and GM-CSF 1 ng/mL or with saturating concentrations of growth factors including IL-3 200 U/mL, erythropoietin 4 U/mL, and stem cell factor (SCF) 100 ng/mL. All growth factors were from Peprotech. Cultures were incubated in a humidified incubator at 37° C. in 5% $CO_2$ for 7 days and were scored for total colonies and for morphology to determine colony forming unit (CFU)-granulocyte-macrophage (GM) or CFU-monocyte (M).

Crystallization of SHP2 with TTN D-1 and X-ray Data Collection.

All crystallization experiments were carried out at room temperature using the hanging drop vapor diffusion method. For co-crystallization, 100 μL of the SHP2 stock (7.0 mg/mL) in 20 mM Tris-HCL (pH 7.5), 50 mM NaCl, 1 mM EDTA, and 3.0 mM DTT was mixed with 1 μL of TTN D-1 stock (50 mM in DMSO). Protein drops were equilibrated against a reservoir solution containing 25% w/v polyethylene glycol 3350, 100 mM sodium chloride, and 100 mM HEPES buffer (pH 7.5). For X-ray data collection, the crystals were transferred into 5 μL of cryoprotectant buffer containing 30% w/v polyethylene glycol 3350, 100 mM NaCl, 1 mM TTN D-1 and 100 mM HEPES (pH 7.5), and were allowed to soak for 30 min. The crystals were then flash-cooled by liquid nitrogen. X-ray data were collected at 19BM beamline at APS (Argonne, Ill.). Data were processed using the program HKL3000 (Otwinowski and Minow, 1997), and the statistics are provided in Table 2.

Structural Determination and Refinement.

The structure of SHP2.TTN D-1 was solved by molecular replacement using the program AMoRe (Navaza, 1994). The apo structure of SHP2 (PDB entry code 3B70) (Ban et al., 2009), without the solvent molecules and first 16 residues, was used as a search model. The resulting difference Fourier map indicated some alternative tracing, which was incorporated into the model. The map revealed the density for the bound TTN D-1 in the SHP2 active site. The structure was refined to 2.3 Å resolution with the program CNS1.1 (Brünger et al., 1998), first using simulated annealing at 2,500 K, and then alternating positional and individual temperature factor refinement cycles. The progress of the refinement was evaluated by the improvement in the quality of the electron density maps, and the reduced values of the conventional R factor ($R=\Sigma_h||F_o|-|F_c||/\Sigma_h|F_o|$), and the free R factor (3.8% of the reflections omitted from the refinement) (Brünger, 1992). Electron density maps were inspected and the model was modified on an interactive graphics workstation with the program O (Jones et al., 1991). Finally, water molecules were added gradually as the refinement progressed. They were assigned in the $F_o-F_c$ difference Fourier maps with a 3σ cutoff level for inclusion in the model. The geometry of the final models was examined with the program PROCHECK (Laskowski et al., 1993). The complex structure had 99.6% of the residues in the allowed regions of the Ramachandran plot.

Example 2

Results

Identification of TTN as a SHP2 Inhibitor.

Given the observed effect of TTN on tyrosine phosphorylation, the inventors explored whether TTN or its structurally related natural products could modulate the catalytic activity of the PTPs, a family of signaling enzymes that work together with protein tyrosine kinases to regulate the cellular level of protein tyrosine phosphorylation (Hunter, 2000; Tonks, 2006). They produced TTN and TTM, along with nine engineered analogs featuring the TTN and TTM scaffolds (FIG. 9; Li et al., 2008; Ju et al., 2009; Li et al., 2009; Luo et al., 2010) and evaluated them as potential modulators of PTP activity. The effect of the compounds on PTP-catalyzed hydrolysis of p-nitrophenyl phosphate (pNPP) was assessed at pH 7 and 25° C. Members of the PTP superfamily that were included in the screen included the cytosolic PTPs, PTP1B, SHP1, SHP2, Lyp, HePTP, Meg2, and FAP1, the receptor-like PTPs, CD45, LAR, and PTPα, the dual specificity phosphatases VHR, VHX, and Cdc14, and the low molecular weight PTP. When assayed at 10 μM concentration, neither TTM nor its analogs exhibited any inhibitory activity against the panel of PTPs. Remarkably, TTN and one of its engineered analogs TTN D-1 (FIGS. 1A-B) reduced SHP2 activity by 80-90% at 10 μM concentration. Importantly, TTN and TTN D-1 were highly specific for SHP2, exhibiting no significant activity (<30% inhibition at 10 μM concentration) toward the rest of the PTP panel.

Figure 2:
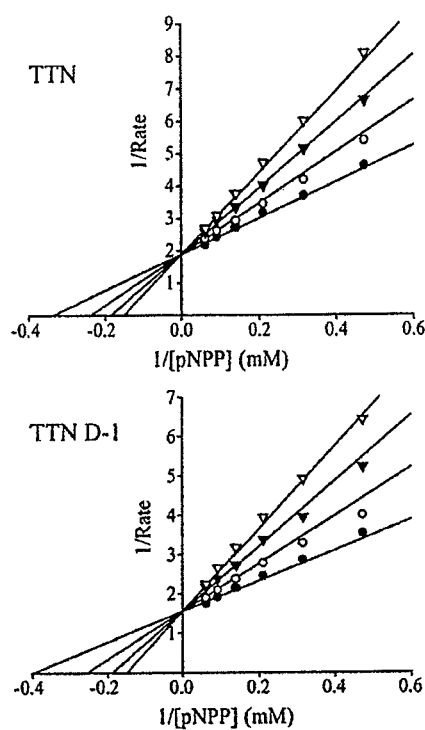
FIG. 2. Lineweaver-Burk plots for TTN and TTN D-1 mediated SHP2 inhibition. TTN concentrations were 0 (●), 1 (○), 2 (▼), and 3 (∇) μM, respectively. TTN D-1 concentrations were 0 (●), 2 (○), 4 (▼), and 6 (∇) μM, respectively.

To further characterize SHP2 inhibition by the TTN and TTN D-1, the $IC_{50}$ values for TTN and TTN D-1 were measured at a pNPP concentration fixed at the experimentally determined $K_m$ for each PTP. Therefore, all of the $IC_{50}$ values reported in this study directly reflect the true affinity of the compound for the enzymes tested. As shown in Table 1, TTN inhibits SHP2 with an $IC_{50}$ of 2.9 μM, while it is less effective toward other PTPs, with an $IC_{50}$ value of 14.6 μM for SHP1, 20 μM for Lyp, 40 μM for PTP1B, and greater than 50 μM for HePTP, PTPci, CD45, VHR and Cdc14. Thus, TTN displays at least a 5-fold preference for SHP2 over all PTPs examined. Similar results were obtained for TTN D-1 (Table 2). To establish the mechanism of SHP2 inhibition by TTN and TTN D-1, the inhibition constants and mode of inhibition were determined by steady-state kinetic analysis of the SHP2-catalyzed reaction. As shown in FIG. 2, TTN and TTN D-1 act as competitive inhibitors of the SHP2-catalyzed reaction, with K, values of 1.6±0.1 μM and 2.3±0.2 μM, respectively. This agrees well with the $IC_{50}$ value determined at the substrate $K_m$. Together, the results indicate that TTN and TTN D-1 represent the most potent and specific SHP2 inhibitors reported to date.

TABLE 2

$IC_{50}$ (μM) of TTN and TTN D-1 for a panel of PTPs

| PTP | TTN | TTN D-1 |
| --- | --- | --- |
| SHP2 | 2.9 ± 0.2 | 4.4 ± 0.4 |
| SHP1 | 14.6 ± 1.1 | 20.7 ± 2.1 |
| PTP1B | 40.0 ± 10 | 28.0 ± 3 |
| Lyp | 20.0 ± 2 | >50 |
| HePTP | >50 | >50 |
| PTPα | >50 | >50 |
| CD45 | >50 | >50 |
| VHR | >50 | >50 |
| Cdc14A | >50 | >50 |

All measurements were made using pNPP as a substrate at pH 7.0, 25° C., and I = 0.15 M.

TTN Blocks SHP2 Mediated Signaling.

TTN induces immunosuppression by suppression of TCR-mediated tyrosine phosphorylation and ERK1/2 activity in T cells (Shim et al., 2002). However, the mechanism of action for TTN's ability to block TCR signaling remains undefined. The inventors hypothesized that TTN may exert its immunosuppressive effect by inhibiting SHP2, as SHP2 is a positive mediator downstream of almost all growth factor and cytokine receptors and its phosphatase activity is required for activation of the Ras/ERK1/2 kinase pathway (Neel et al., 2003). Indeed, SHP2 deletion has been shown to cause decreased TCR signaling and impaired ERK1/2 activation in T cells (Nguyen et al., 2006). Given the observed potency and selectivity of TTN and TTN D-1 toward SHP2, the inventors proceeded to evaluate their ability to inhibit SHP2-dependent signaling inside the cell. Previous studies showed that TTN inhibits human primary T-cell tyrosine phosphorylation at 1 μg/mL (1.65 μM) concentration (Shim et al., 2002), which is close to the measured $K_i$ value of TTN for SHP2. They found that at similar concentrations (2-4 μM), TTN efficiently attenuated TCR-mediated tyrosine phosphorylation in Jurkat T cells (FIG. 3A and FIG. 10). Importantly, TTN D-1 also blocked TCR-mediated tyrosine phosphorylation whereas TTM, which does not inhibit SHP2 activity, had no effect on tyrosine phosphorylation in Jurkat cells. Furthermore, TTN and TTN D-1 also strongly reduced the TCR-mediated ERK1/2 activation whereas TTM elicited no appreciable change in ERK1/2 phosphorylation level (FIG. 3B and FIG. 10). Moreover, II-B08, a structurally unrelated small molecule inhibitor of SHP2 (Zhang et al., 2010), is also capable of inhibiting anti-CD3-induced tyrosine phosphorylation and ERK1/2 activation in Jurkat T cells (FIG. 11), providing further evidence that the effect of TTN and TTN D-1 on TCR-mediated signaling was due at least in part to inhibition of SHP2.

To further establish SHP2 as a cellular target for TTN, the inventors also studied the effect of TTN on several cellular processes mediated by SHP2. Germline SHP2 mutations are commonly found in the congenital disorder, Noonan syndrome, and somatic gain-of-function SHP2 mutations are frequently observed in the childhood leukemia, juvenile myelomonocytic leukemia (JMML), as well as in childhood and adult acute myeloid leukemia and various solid tumors (Tartaglia and Gelb, 2005; Chan et al., 2008). Peripheral blood hematopoietic progenitors from JMML patients are hypersensitive to the cytokine granulocyte-macrophage colony-stimulating factor (GM-CSF) (Emanuel et al., 1991). They showed previously that introduction of gain-of-function SHP2 mutations (SHP2/D61Y and SHP2/E76K) into hematopoietic progenitors induces hypersensitivity to GM-CSF (Chan et al., 2005), hyperactivation of GM-CSF-stimulated ERK1/2, and skewed monocytic differentiation (Chan et al., 2005; Yang et al., 2009). Based on these findings, they hypothesized that treatment of mutant SHP2-bearing hematopoietic progenitors with TTN would attenuate GM-CSF-stimulated hyperproliferation, ERK1/2 hyperactivation, and skewed monocytic differentiation.

Figure 4:
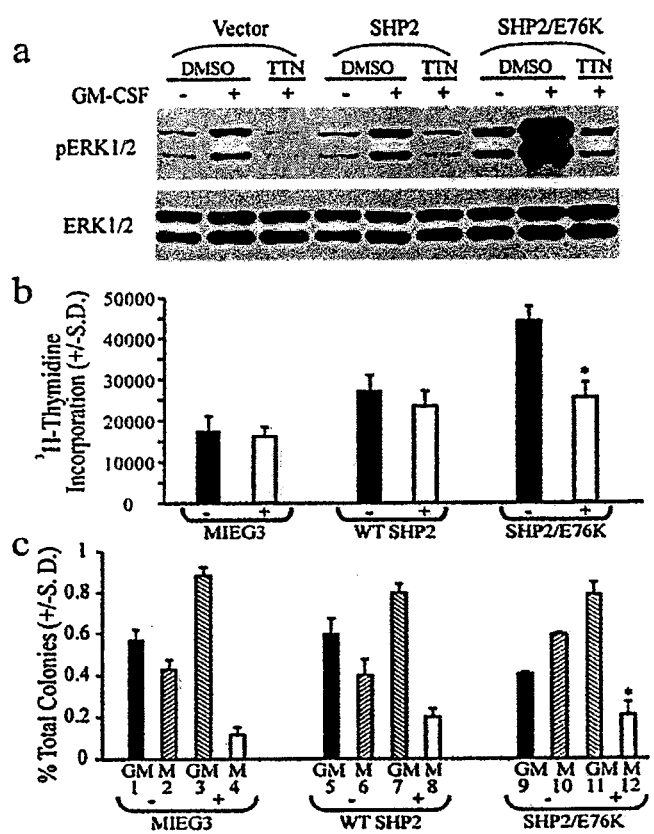
FIGS. 4A-C. Effect of TTN on SHP2-mediated processes in hematopoietic progenitors.

For biochemical studies, macrophage progenitor cells expressing empty vector (MIEG3), wild-type SHP2, or SHP2/E76K were serum- and growth factor-deprived for 24 hours. Cells were pre-treated with DMSO or 2 μM TTN for 2 hours, and then cultures either remained unstimulated or were stimulated with GM-CSF at 50 ng/mL for 60 minutes. As predicted, TTN abrogated the GM-CSF induced ERK1/2 activation in macrophage progenitors as well as effectively inhibited the ERK1/2 hyperactivation in the SHP2/E76K-expressing cells (FIG. 4A). They next examined the effect of TTN on GM-CSF-stimulated hyperproliferation of SHP2/E76K-expressing hematopoietic progenitors. Cells were serum- and growth factor-deprived for 6 hrs and then cultured in complete medium with GM-CSF (1 ng/mL) in the presence or absence of 2 μM TTN for 24 hrs and pulsed with [$^3$H] thymidine to measure proliferation. As previously observed, in response to low GM-CSF stimulation, the SHP2/E76K-expressing progenitors hyperproliferated compared to the MIEG3- or WT SHP2-expressing progenitors (Chang et al., 2005; Yang et al., 2008), and TTN effectively reduced the proliferation of SHP2/E76K-expressing progenitors (FIG. 4B). Under these conditions, the progenitors expressing SHP2/E76K appear to be more sensitive to TTN compared to those expressing MIEG3 or wild-type SHP2. Additionally, as previously observed (Yang et al., 2008; Yang et al. 2009), a significantly greater number of colony forming unit-macrophage (CFU-M) were generated from progenitors expressing SHP2/E76K, with a concomitant reduction in CFU-granulocyte/macrophage (CFU-GM) compared to progenitors transduced with MIEG3 or wild-type SHP2 (FIG.

4C, compare #9/10 to #5/6 and #1/2). However, when plated in the presence of 2 μM TTN, the development of CFU-M was reduced in all cells types and, notably, the progenitor colony type distribution for the SHP2/E76K-expressing cells was similar to the MIEG3- and wild-type SHP2-expressing cells in the presence of TTN (FIG. 4C, compare No. 11/12 to #7/8 and #3/4). Collectively, these findings indicate that i) TTN inhibits SHP2-dependent signaling, ii) inhibition of SHP2 phosphatase activity with TTN effectively reduces ERK1/2 activation, and iii) TTN, under specified conditions, selectively reduces proliferation and normalize differentiation of mutant SHP2-expres sing hematopoietic cells. Structural basis of TTN/TTN D-1 specificity for SHP2. To provide further evidence that SHP2 is a molecular target of TTN, the inventors determined the X-ray crystal structure of SHP2 in complex with TTN D-1, as crystallization attempts for the SHP2-TTN complex were unsuccessful. The structure of SHP2.TTN D-1 was solved by molecular replacement, using the apo-form of SHP2 catalytic domain as the search model (Barr et al., 2009), and refined to a crystallographic R-factor of 17.0% ($R_{free}$ 22.2%) at 2.3 Å resolution. Table 3 summarizes data collection and refinement statistics. The atomic model of SHP2.TTN D-1 includes one protein monomer in an asymmetric unit, which contains residues 262-313, 325-526 and all atoms of TTN D-1. The structure of SHP2.TTN D-1 is similar to the apo structure used for molecular replacement modeling, with an overall root-mean-square-derivation (RMSD) of 0.38 Å between all Cα atoms. The existence of TTN D-1 in the complex was revealed by Fo–Fc difference map and confirmed by 2Fo–Fc electron density map after refinement (FIG. 5A). Unambiguous electron densities were observed for all surface loops, including the PTP signature motif or the P-loop (residues 458-465, which harbors the active site nucleophile C459 and R465 for recognition of the phosphoryl moiety in the substrate), the pTyr recognition loop (residues 277-284, which confers specificity to pTyr), the WPD loop (residues 421-431, which contains the general acid-base catalyst D425), and the Q-loop (residues 501-507, which contains the conserved Q506 required to position and activate a water molecule for hydrolysis of the phosphoenzyme intermediate) (Zhang, 2003).

TABLE 3

Crystallographic Data/Refinement Statistics for SHP2•TTN D-1 Complex

| Data Collection | |
| --- | --- |
| Space group | P2$_1$ |
| Cell Dimensions | |
| a (Å) | 39.5 |
| b (Å) | 76.0 |
| c (Å) | 48.4 |
| β (deg) | 98.9 |
| Resolution range (Å) | 50.00-2.30 |
| Highest resolution shell (Å) | 2.38-2.30 |
| Unique observations | 12,544 |
| Completeness (%) | 97.5 (74.6)[a] |
| Redundancy | 3.6 |
| $R_{merge}$ (%)[b] | 5.6 (25.2)[a] |
| <I>/<σI> | 19.7 (2.5)[a] |
| Refinement | |
| Resolution range (Å) | 50.00~2.30 |
| No. of reflections used (F ≥ 1.5σF) | 11,753 |
| $R_{work}^c/R_{free}^d$ (%) | 16.7/21.5 |
| No. of atoms | |
| protein | 2,070 |
| inhibitor (1 molecule) | 46 |
| Waters | 156 |

TABLE 3-continued

Crystallographic Data/Refinement Statistics for SHP2•TTN D-1 Complex

| RMS deviations from ideal | |
| --- | --- |
| bonds (Å) | 0.0058 |
| angles (deg) | 1.17 |
| Average B-factor (Å$^2$) | 31.9 |
| Ramachandran plot (%) | |
| Allowed | 99.6 |
| not allowed | 0.4 |

$^a$The value in parentheses corresponds to the highest resolution shell.
$^b\text{R}_{merge} = \Sigma_h \Sigma_i |\text{I}(h)_i - <\text{I}(h)>|/\Sigma_h \Sigma_i \text{I}(h)_i$.
$^c\text{R}_{work} = \Sigma_h |\text{F}(h)_{calcd} - \text{F}(h)_{obsd}|/\Sigma_h \text{F}(h)_{obsd}$, where F(h)$_{calcd}$ and F(h)$_{obsd}$ were the refined calculated and observed structure factors, respectively.
$^d\text{R}_{free}$ was calculated for a randomly selected 3.8% of the reflections that were omitted from refinement.

Figure 1:
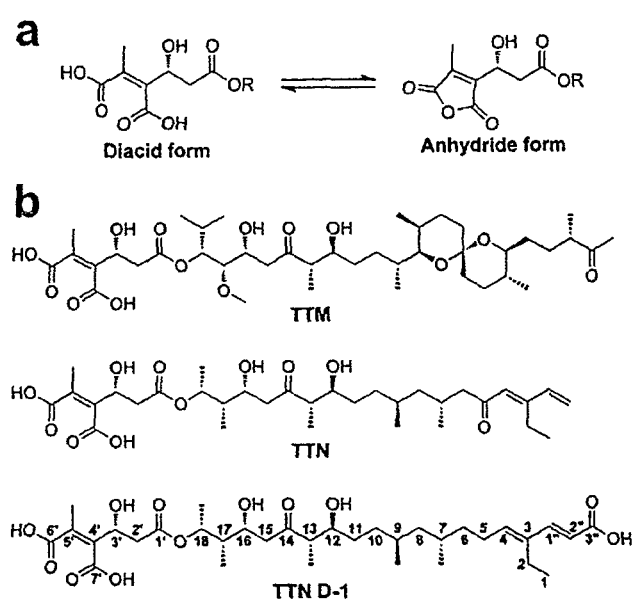
FIGS. 1A-B. Structures of TTN and TTM compounds.

Under neutral conditions, both TTM and TTN exist as equilibrating mixtures of two interconverting anhydride and diacid forms in an approximately 5:4 ratio (Cheng et al., 1987; Cheng et al., 1990a; Cheng et al., 1990b) (FIG. 1A). As shown in FIG. 5A, TTN D-1 binds to SHP2 in an extended conformation, with the diacid moiety penetrating into SHP2 active site. This is consistent with TTN and TTN D-1 being competitive inhibitors of SHP2 (FIG. 2). Interestingly, if the structure of phosphopeptide-bound SHP1 (Yang et al., 2001), a close homolog of SHP2, predicts the orientation of substrate peptide binding to SHP2, then the polyketide backbone of TTN D-1 in this structure occupies exactly where substrate residues N-terminal to pTyr would otherwise bind in SHP2 (FIG. 5B). Superimposition of the SHP1.phosphopeptide structure onto the SHP2.TTN D-1 structure reveals that the diacid moiety is localized at almost the same position of pTyr, and the remaining polyketide backbone of TTN D-1 occupies the substrate-binding groove defined by I282, Y279, R278, Q335, K364, S365, L334 and V368. Thus, the binding mode of TTN D-1 mimics that of pTyr peptide substrates.

A rich network of interactions is responsible for the precise positioning of TTN D-1 in the complex (FIGS. 6A-C). The TTN D-1 diacid is anchored via four direct and three water-mediated hydrogen bonds with SHP2 active site residues R465, A461, 5460, Q510, and K$_{366}$, consistent with the diacid form as the active isomer for SHP2 inhibition. Specifically, the carboxylate group attached to C6' makes two H-bonds with the main-chain amides of A461 and R465 in the P-loop, and also engages in polar interactions with the main chain of 5460 as well as side chains of K366 and Q510, which are mediated by waters W1 and W2. One of the C7' carboxylate oxygen interacts directly with the side chains of 5460 and K366, and also forms a H-bond with W1 which is stabilized by the main chain amide at residue 5460, the side chain of K366, and one of the carboxylate oxygen at C6'.

In addition to the polar interactions between the diacid head group and SHP2 active site, the rest of the TTN D-1 molecule is primarily involved in hydrophobic interactions with SHP2 (FIGS. 6A-C). The methyl group connected to C5' sits within a hydrophobic pocket consisting of A461, I463, I282, and Q506, which further tighten-up the interaction of the diacid moiety with SHP2 active site. The polyketide backbone bends around the phenyl ring of Y279 and makes Van der Waals contacts with a number of residues lining the hydrophobic groove. These include interactions between the phenyl side chain of Y279 and carbon atoms from C1' to C13; Cα, Cβ and Cγ of R278 with C8, C11 and C12; K364 with the methyl group on C17; L334 with the methyl group on C7; S365 and V368 with C1 and C2, and Q335 with the acrylic acid tail. Finally, the terminal carboxylate at C3" is bound primarily through a H-bond with the side chain of Q335.

These biochemical and cellular data indicate that TTN and TTN D-1 exhibit similar affinity for SHP2. As shown in FIGS. 1A-B, TTN differs from TTN D-1 only in the very right end portion of the molecule with TTN D-1 bearing an extra carboxyl group at C3" but lacking the ketone at C5 (FIGS. 1A-B). This suggests that the left-hand side of these compounds is essential for SHP2 inhibition but the end of the right-half is exchangeable. Indeed, the structure of SHP2.TTN D-1 reveals that binding of TTN D-1 to SHP2 is dominated by the left 2/3 of TTN D-1, which is identical in TTN (FIGS. 6A-B). Molecular modeling indicates that a new polar interaction could form between the C5 carbonyl in TTN and the side chain of R278, which may compensate for the lost polar interaction between Q335 and C3"-COOH in TTN D-1.

In addition to revealing a molecular mechanism for SHP2 inhibition by TTN D-1 and TTN, the structure of the SHP2.TTN D-1 complex also provide a potential explanation for the inactivity of TTM toward SHP2. The major structural differences between TTM and TTN reside in the region distal to the diacid moiety (FIGS. 1A-B). Assuming that the left-half of the TTM molecule binds SHP2 in the same manner as TTN D-1 does, the rigid and twisted spiroketal moiety will experience severe steric clash with residues R278 and L334. This illustrates why TTM and analogs lack SHP2 inhibitory activity. Finally, the structure of the SHP2.TTN D-1 complex identifies 18 SHP2 residues involved in binding TTN D-1 (FIG. 6C). Although many of the residues important for TTN D-1 recognition are not unique to SHP2, no single PTP has the same combinations of all contact residues, which suggest that the binding surface defined by these residues in SHP2 is unique and likely responsible for the observed TTN/TTN D-1 selectivity.

Example 3

DISCUSSION

The immunosuppressive activity exhibited by TTN differs from other bacteria and fungi derived immunosuppressive drugs such as cyclosporin A (CsA), FK506 (tacrolimus), and rapamycin (Gerber et al., 1998). CsA and FK506 exert their pharmacological effects by binding to endogenous proteins called immunophilins, and the immunophilin and drug complex inhibits the activity of the serine/threonine protein phosphatase calcineurin (PP2B) (Liu et al., 1991), which is activated when intracellular calcium level rises upon T cell activation (Flanagan et al., 1991; Bierer et al., 1990). Similar to FK506, rapamycin also binds to the FK506-binding protein family of immunophilins. However, the complex of rapamycin/FK506-binding protein has no effect on calcineurin activity but instead blocks the TOR (target of rapamycin) pathway triggered by the IL-2 receptor Chung et al., 1992; Kuo et al., 1992). In contrast, the immunosuppressive activity TTN results from its ability to block tyrosine phosphorylation of intracellular signaling molecules downstream of the TCR (Shim et al., 2002). Unfortunately, the mechanistic basis of TTN's immunosuppressive activity remains to be established.

Originally isolated as antifungal antibiotics, the only known mechanism of the observed activities for TTN and its structurally related natural product TTM are their ability to inhibit serine/threonine protein phosphatases PP1 and PP2A (MacKintosh and Klumpp, 1990; Mitsuhashi et al., 2001). Since TTM does not elicit any immunosuppressive activity (Shim et al., 2002), it is unlikely that TTN's immunosuppressive activity results from PP1 or PP2A inhibition. Instead, a yet unidentified molecular target may be required to explain the immunosuppressive activity of TTN. In this study, the inventors establish that TTN and its engineered analog TTN D-1 are potent and competitive SHP2 inhibitors. They provide evidence that TTN and TTN D-1 block tyrosine phosphorylation and ERK activity in T cells and attenuate gain-of-function SHP2-induced hematopoietic progenitor hyperproliferation and monocytic differentiation. In addition, the obtained a crystal structure of SHP2 with TTN D-1 bound to its active site, which offers molecular insights into the origin of TTN/TTN D-1 selectivity for SHP2. Collectively, the biochemical, cellular and structural data support the notion that SHP2 is a cellular target for TTN, and furnish a plausible mechanism for TTN's observed immunosuppressive and anticancer activity.

Protein tyrosine phosphorylation is the key cellular event that controls TCR signaling. The Src family kinases are responsible for tyrosine phosphorylation of intracellular signaling molecules downstream of the TCR (Brdicka et al., 2005). SHP2 exerts a positive effect on cell signaling, and is required for Src and Ras-ERK1/2 activation downstream of most growth factor and cytokine receptors, including TCR (Neel et al., 2003; Tiganis and Bennett, 2007; Nguyen et al., 2006). SHP2 can activate the Src kinases by dephosphorylating Csk (C-terminal Src kinase) binding protein Cbp/PAG, which prevents the access of Csk (which inactivates Src) to the Src kinases (Zhang et al., 2004). Ras activation by SHP2 involves SHP2 catalyzed dephosphorylation of tyrosine-phosphorylated sites of receptor molecules that bind p120 RasGAP (Agazie and Hayman, 2003) and Sprouty (Hanafusa et al., 2004), a negative regulator of Ras. Thus, the observed decrease in TCR-induced tyrosine phosphorylation and ERK1/2 activation by TTN is fully consistent with TTN being an inhibitor of SHP2. However, this does not exclude the possibility that other targets (e.g. PP1 and PP2A) may also contribute to TTN's biological activities. In this regard, the inventors note that although TTN inhibits PP1 and PP2A in the low nM range in biochemical assays, often 1-5 μM concentrations of TTN are required to exert a cellular effect (Luo et al., 2007; Mitsuhashi et al., 2003; Mitsuhashi et al., 2008). As shown in this study, TTN at this concentration range will also inhibit SHP2 activity. Future investigation with more potent and selective small molecule probes will be required to resolve whether TTN's immunosuppressive effect results primarily from SHP2 inhibition.

The PTP family provides an exciting array of validated (Zhang et al., 2001) but previously deemed undruggable diabetes/obesity, autoimmunity and oncology targets. Identification of the polyketide natural product TTN as a SHP2 inhibitor has profound implication in drug discovery targeting the PTPs, which have proven to be exceptionally challenging targets for the development of new therapeutic agents. The main problem is poor membrane permeability and lack of cellular efficacy of existing PTP inhibitors, which have limited further advancement of such compounds as drug candidates (Zhang and Zhang, 2007). Bioactive natural products are very promising leads for drug development because they are evolutionarily selected and validated for interfering and interacting with biological targets. Given its excellent in vivo activity, TTN serves as a promising lead for the development of more potent and specific SHP2 inhibitors. To this end, the crystal structure of SHP2 bound to TTN D-1 should facilitate structure-based design effort based on the TTN scaffold.

The fact that TTN is of microbial origin should greatly ease the concern to produce the complex natural product lead and generate its structural analogs for further mechanistic studies and clinical developments. Thus, promising leads of complex microbial natural products can be produced by large-scale fermentation, thereby significantly reducing production cost and environmental concerns. Furthermore, one of the inventors has recently cloned and characterized the biosynthetic gene cluster for TTN in *S. griseochromogenes* (Li et al., 2009). Judicial application of the combinatorial biosynthetic strategies to the TTN biosynthetic machinery for TTN analogs has already been demonstrated (Lou et al., 2010), as exemplified by the discovery of TTN D-1 as an SHP2 inhibitor in this study. Taken together, the current study sets an outstanding stage to rationally engineer the TTN biosynthetic machinery, guided by the SHP2.TTN D-1 structure, for the development of novel analogs, some of which could be further exploited as SHP2-specific inhibitors for clinical application in immunosuppression and cancer.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

X. References

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

U.S. Pat. No. 4,551,433
U.S. Pat. No. 5,220,007
U.S. Pat. No. 5,221,605
U.S. Pat. No. 5,238,808
U.S. Pat. No. 5,284,760
U.S. Pat. No. 5,354,670
U.S. Pat. No. 5,366,878
U.S. Pat. No. 5,380,721
U.S. Pat. No. 5,389,514
U.S. Pat. No. 5,635,377
U.S. Pat. No. 5,789,166
U.S. Pat. No. 5,798,208
U.S. Pat. No. 5,830,650
Agazie and Hayman, *Mol. Cell. Biol.*, 23:7875-7886, 2003.
Barr et al., *Cell*, 136:352-363, 2009.
Bierer et al., *Proc. Natl. Acas. Sci. USA*, 87:9231-9235, 1990.
Blackburn et al., *J. Lipid. Res.*, 32(12):1911-1918, 1991.
Boothman et al., *Cancer Res.*, 49(11):2871-2878, 1989.
Borek, *Carcinog. Compr. Surv.*, 10:303-316, 1985.
Braisted and Wells, *Proc. Natl. Acad. Sci. USA*, 93(12):5688-5692, 1996.
Brdicka et al., *Mol. Cell. Biol.*, 25:4924-4933, 2005.
Brünger et al., *Acta Crystallogr. D.*, 54:905-921, 1998.
Brünger, *Nature*, 355:472-475, 1992.
Burks et al., *Proc. Natl. Acad. Sci. USA*, 94(2):412-417, 1997.
Burton and Barbas, *Adv. Immunol.*, 57:191-280, 1994.
Cadwell and Joyce, *PCR Methods Appl.*, 2(1):28-33, 1992.
Chan et al., *Blood* 105, 3737-3742, 2005.

Chan et al., *Cancer and Metastasis Rev.*, 27179-192, 2008.
Cheng et al. *J. Antibiot.*, 43:809-819, 1990a.
Cheng et al. *J. Antibiot.*, 43:890-896, 1990b.
Cheng et al., *J. Antibiot.*, 40:907-909, 1987.
Cheng et al., *J. Antibiot.*, 42:141-144, 1989.
Cheng et al., *J. Bacteriol.*, 184:7013-7024, 2002.
Cheng et al., *Proc. Natl. Acad. Sci. USA*, 100(6):3149-3154, 2003.
Chung et al., *Cell*, 69:1227-1236, 1992.
Cooley et al., *Science*, 239(4844):1121-1128, 1988.
Cunningham and Wells, *Science*, 244(4908):1081-1085, 1989.
Emanuel et al., *Blood*, 77:925-929, 1991.
Flanagan et al., *Nature*, 352:803-807, 1991.
Gerber et al., *Transplant. Proc.*, 30:1573-1579, 1998.
Gramajo et al., *J. Bacteriol.*, 173:6475-6483, 1991.
Grim et al., *Gene*, 151:1-10, 1994.
Guilfoile & Hutchinson, *Proc. Natl. Acad. Sci. USA*, 88:8553-8557, 1991.
Hall, *Genetics*, 120(4):887-897, 1988.
Han et al., *Transplant Proc.*, 35:547, 2003.
Hanafusa et al., *J. Biol. Chem.*, 279:22992-22995, 2004.
Hilton et al., *J. Appl. Bacteriol.*, 81(6):575-584, 1996.
Hopwood and Sherman, *Ann. Rev. Geneet.*, 24:37-66, 1990.
Hopwood et al., *Meth. Enzymol.*, 153:116-166, 1987.
Huang et al., *Nucl. Acids Res.*, 24:4202-4209, 1996.
Hunter, *Cell*, 100:113-127, 2000.
Jones et al., *Acta Crystallogr. A.*, 47:110-119, 1991.
Ju et al., *Org. Lett.*, 11:1639-1642, 2009.
Kao et al., *Science*, 265:509-512, 1994.
Kuo et al., *Nature*, 358:70-73, 1992.
Lambert and Borek, *J. Natl. Cancer Inst.*, 80(18):1492-1497, 1988.
Laskowski et al., *J. Appl. Crystallogr.*, 26:283-291, 1993.
Lee et al., *Mol. Cancer. Ther.*, 5:3222-3231, 2006.
Li et al., *J. Biol. Chem.*, 283:28607-28617, 2008.
Li et al., *J. Natl. Prod.*, 72:450-459, 2009.
Liu et al., *Cell*, 66:807-815, 1991.
Luo et al., *EMBO J.*, 26:1511-1521, 2007.
Luo et al., *J. Am. Chem. Soc.*, 132(19):6663-6671, 2010.
MacKintosh and Klumpp, *FEBS Lett.*, 277:137-140, 1990.
McCann et al., *Proc. Natl. Acad. Sci. USA*, 72(3):979-983, 1975.
Mitsuhashi et al., *Biochem. Biophys. Res. Commun.*, 287: 328-331, 2001.
Mitsuhashi et al., *Int. J. Oncol.*, 33:1027-1035, 2008.
Mitsuhashi et al., *J. Biol. Chem.*, 278:82-88, 2003.
Motamedi and Hutchinson, *Proc. Natl. Acad. Sci. USA*, 84:4445-4449, 1987.
Munugalavadla et al., *Blood*, 110:1612-1620, 2007.
Navaza, *Acta Crystallogr. A.*, 50:157-163, 1994.
Neel et al., *Trends Biochem. Sci.*, 28:284-293, 2003.
Nguyen et al., *J. Immunol.* 177:5990-5996, 2006.
O'Hagan, In: *The Polyketide Metabolites*, Ellis Horwood Ltd., 1991.
Oppenheimer et al., *Cell*, 67(3):483-493, 1991.
Osoegawa et al., *Genomics*, 52:1-8, 1998.
Otwinowski and Minow, *Methods Enzymol.*, 276:307-326, 1997.
Pieper et al., *J. Am. Chem. Soc.*, 117:11373-11374, 1995.
Pleper et al., *Nature*, 378:263-266, 1995.
Remington's Pharmaceutical Sciences, 15th Ed., 33:624-652, 1990.
Remington's Pharmaceutical Sciences, 18th Ed. Mack Printing Company, 1289-1329, 1990.
Sambrook et al., Molecular Cloning: A Laboratory Manual, Cold Springs Lab., New York, 1989.
Shen and Hutchinson, *J. Biol. Chem.*, 269:30726-30733, 1994.
Shim et al., *Proc. Natl. Acas. Sci. USA*, 99:10617-10622, 2002.
Stutzman-Engwall and Hutchinson, *Proc. Natl. Acad. Sci. USA*, 86:3135-3139, 1989.
Tang et al., *Chem. Biol.*, 11:33-45, 2004.
Tartaglia and Gelb, *Annu. Rev. Genomics Hum. Genet.*, 6:45-68, 2005.
Tiganis and Bennett, *Biochem. J.*, 402:1-15, 2007.
Tonks, *Nat. Rev. Mol. Cell. Biol.*, 7:833-846, 2006.
Vara et al., *J. Bacteriol.*, 171:5872-5881, 1989.
Wang et al., *Cell*, 111(7):1027-1039, 2002.
Warren et al., *Biochemistry*, 35(27):8855-8862, 1996.
Weissman and Leadlay, *Nat. Rev. Microbiol.*, 3:925-936, 2005.
Wells et al., *J. Leukoc. Biol.*, 59(1):53-60, 1996.
Witte et al., *Cancer Res.*, 49(18):5066-5072, 1989.
Woon et al., *Genomics*, 50:306-316, 1998.
Yang et al., *Exp. Hematol.*, 36:1285-1296, 2008.
Yang et al., *Mol. Cell. Biol.*, 29:4376-4393, 2009.
Yang et al., *J. Biol. Chem.*, 275:4066-4071, 2001.
Yelton et al., *J. Immunol.*, 155(4):1994-2004, 1995.
Zeng et al., *Biochemistry*, 35(40):13157-13164, 1996.
Zhang and Zhang, *Drug Discovery Today*, 12:373-381, 2007.
Zhang et al., *J. Med. Chem.*, 53:2482-2493, 2010.
Zhang et al., *Mol. Cell*, 13:341-355, 2004.
Zhang, *Curr. Opin. Chem. Biol.*, 5:416-423, 2001.
Zhang, *Prog. Nucleic Acid Res. & Mol. Biol.*, 73:171-220, 2003.

What is claimed:

1. A method of treating a SHP2-related cancer in a subject comprising contacting a SHP2-related cancer cell with an analog of tautomycetin thereof, wherein said analog has the structure:

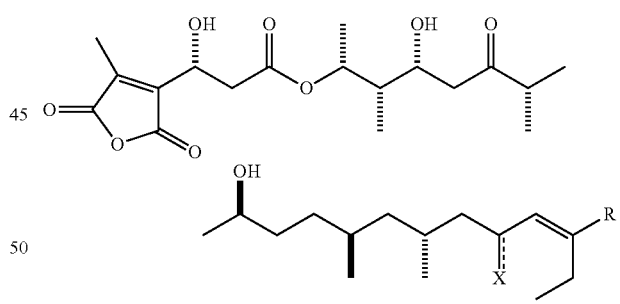

wherein X═O, OH or H, and R═(CH)$_2$COOH or CH(OH)CH$_2$COOH.

2. The method of claim 1, wherein X is ═OH.
3. The method of claim 1, wherein X is ═O.
4. The method of claim 1, wherein said compound is:

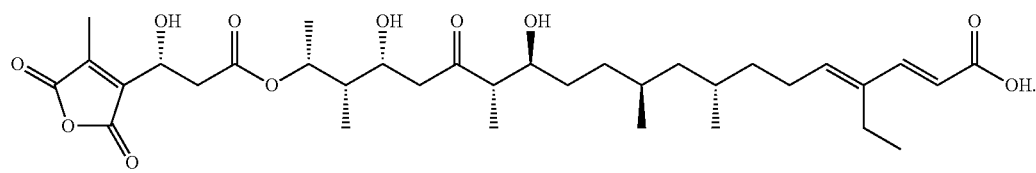 [SMILES: CCC(/C=C/C(=O)O)=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

5. The method of claim 1, wherein said compound is:

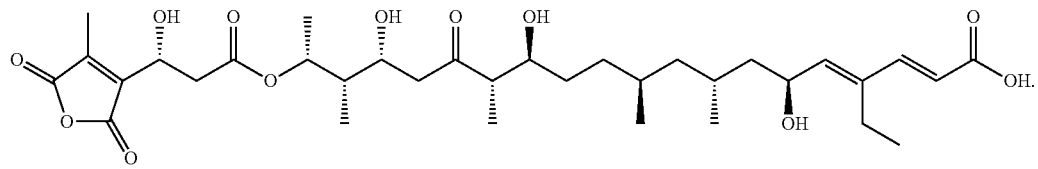

6. The method of claim 1, wherein said compound is:

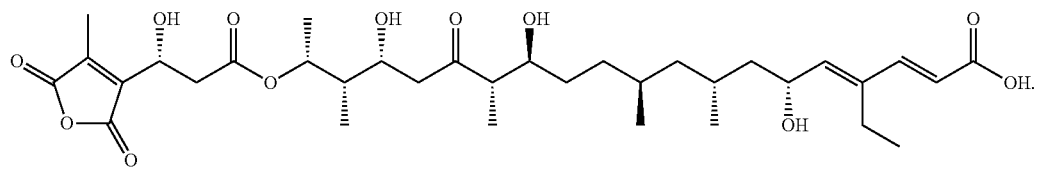 [SMILES: CCC(/C=C/C(=O)O)=C\[C@H](O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

7. The method of claim 1, wherein said compound is:

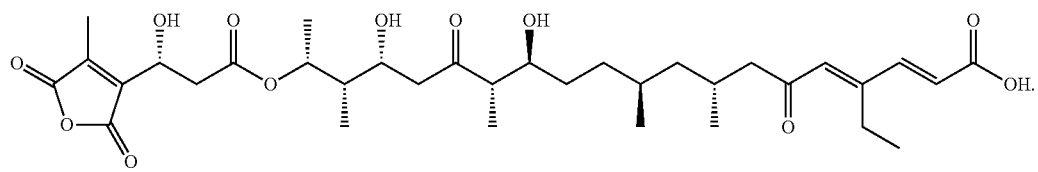 [SMILES: CCC(/C=C/C(=O)O)=C\C(=O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

8. The method of claim 1, wherein said compound is:

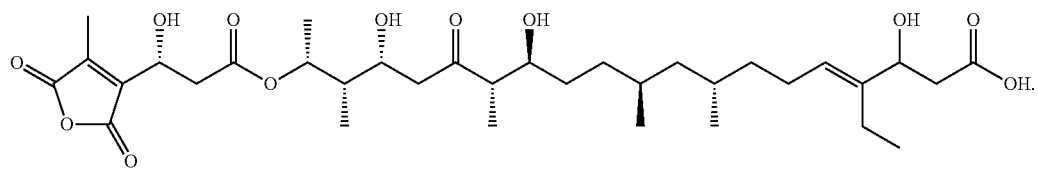 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

9. The method of claim 1, wherein X is H.

10. The method of claim 1, wherein said SHP2-related cancer is not colorectal cancer.

11. The method of claim 1, wherein said SHP2-related cancer is not leukemia.

12. The method of claim 1, further comprising contacting said cancer cell with a second anti-cancer therapy.

13. The method of claim 12, wherein said second anti-cancer therapy is selected from radiotherapy, chemotherapy, immunotherapy, chemotherapy and gene therapy.

14. The method of claim 1, wherein said cancer is multi-drug-resistant, recurrent or metastatic.

15. The method of claim 1, wherein said subject is a human.

16. The method of claim 1, further comprising assessing a cancer cell from said subject for a mutation in SHP2.

17. A method of treating Noonan syndrome comprising administering to a subject an analog of tautomycetin thereof, wherein said analog has the structure:

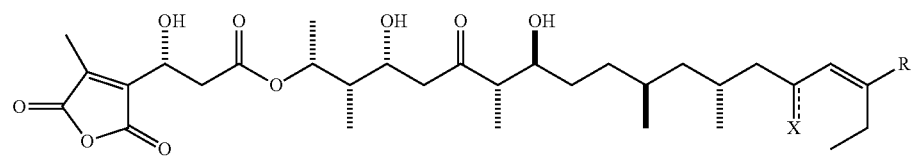

wherein X=O, OH or H, and R=(CH)₂COOH or CH(OH)CH₂COOH.

18. The method of claim 17, wherein said subject is treated with tautomycetin.

19. The method of claim 17, further comprising assessing a cancer cell from said subject for a mutation in SHP2.

20. A method of treating Leopard syndrome comprising administering to a subject an analog of tautomycetin thereof, wherein said analog has the structure:

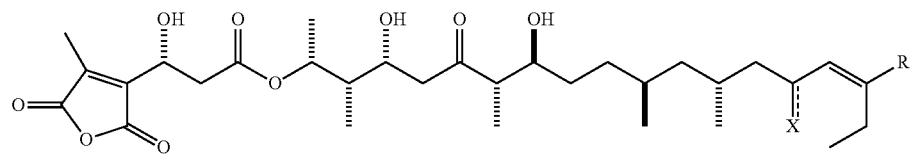

wherein X=O, OH or H, and R=(CH)₂COOH or CH(OH)CH₂COOH.

21. The method of claim 20, wherein said subject is treated with tautonycetin.

22. The method of claim 20, further comprising assessing a cancer cell from said subject for a mutation in SHP2.

23. The method of claim 17, wherein X is H.

24. The method of claim 17, wherein X is —OH.

25. The method of claim 17, wherein X is =O.

26. The method of claim 17, wherein said compound is:

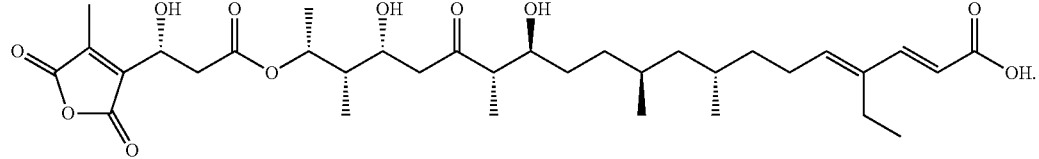 [SMILES: CCC(/C=C/C(=O)O)=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

27. The method of claim 17, wherein said compound is:

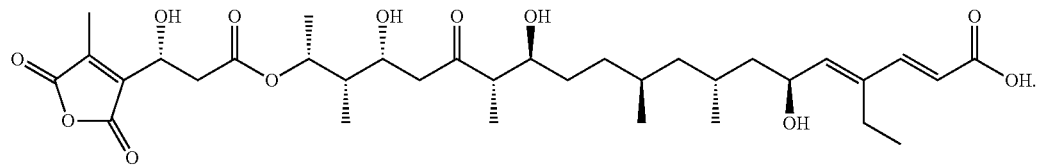 [SMILES: CCC(/C=C/C(=O)O)=C\[C@@H](O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

28. The method of claim 17, wherein said compound is:

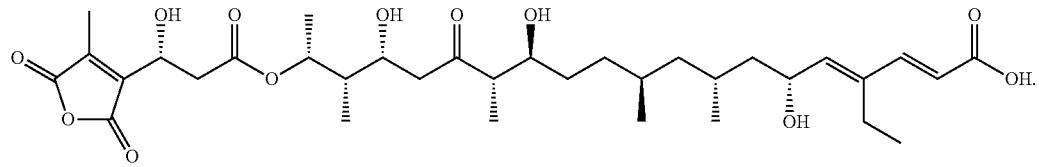 [SMILES: CCC(/C=C/C(=O)O)=C\[C@H](O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

29. The method of claim 17, wherein said compound is:

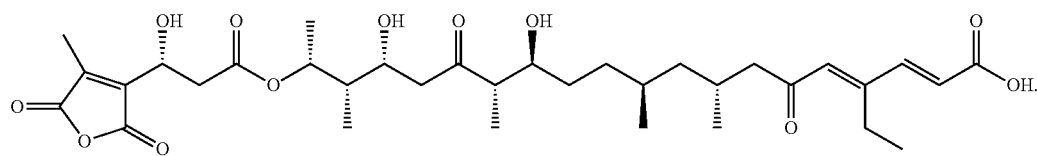

30. The method of claim 17, wherein said compound is:

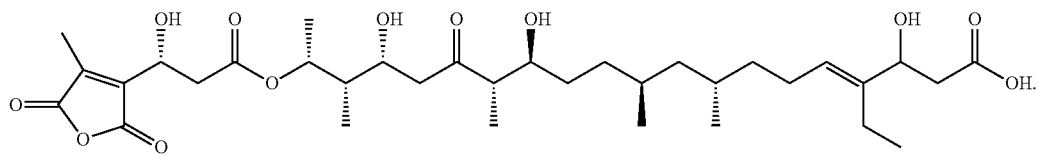 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

10

31. The method of claim 20, wherein X is H.
32. The method of claim 20, wherein X is —OH.
33. The method of claim 20, wherein X is =O.
34. The method of claim 20, wherein said compound is:

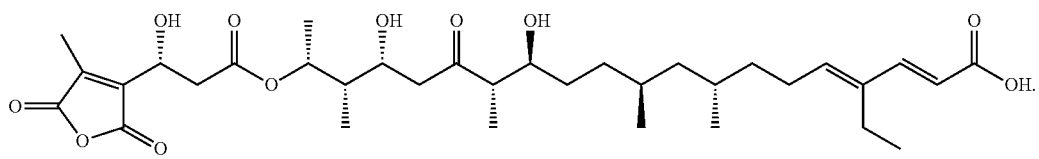 [SMILES: CCC(/C=C/C(=O)O)=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

35. The method of claim 20, wherein said compound is:

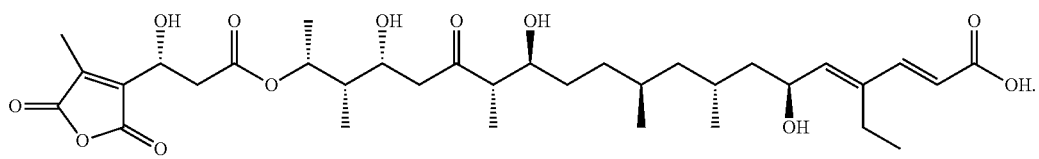 [SMILES: CCC(/C=C/C(=O)O)=C\[C@@H](O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

36. The method of claim 20, wherein said compound is:

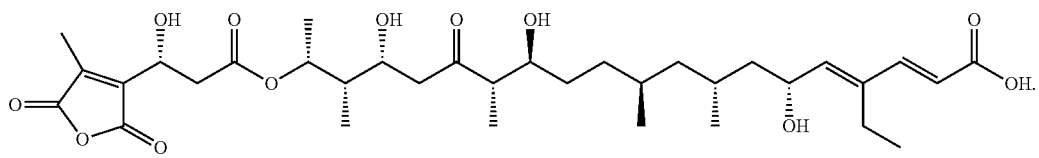 [SMILES: CCC(/C=C/C(=O)O)=C\[C@H](O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

37. The method of claim 20, wherein said compound is:

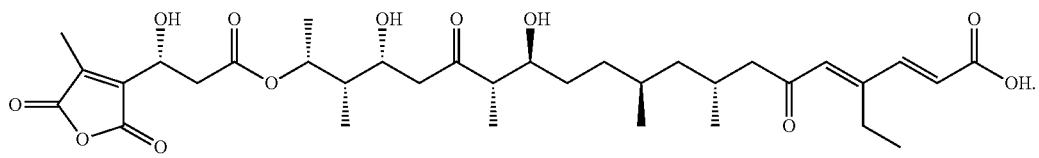 [SMILES: CCC(/C=C/C(=O)O)=C\C(=O)C[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O]

38. The method of claim 20, wherein said compound is:

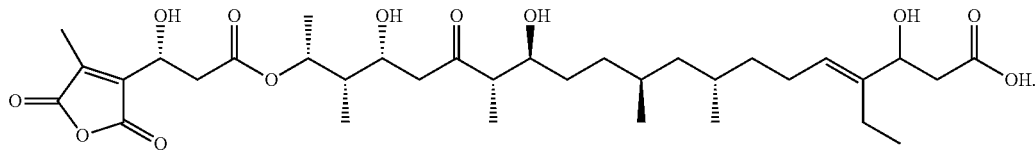 [SMILES: CC/C(=C\CC[C@H](C)C[C@@H](C)CC[C@H](O)[C@H](C)C(=O)C[C@@H](O)[C@H](C)[C@@H](C)OC(=O)C[C@@H](O)C1=C(C)C(=O)OC1=O)C(O)CC(=O)O]

* * * * *

UNITED STATES PATENT AND TRADEMARK OFFICE
CERTIFICATE OF CORRECTION

PATENT NO. : 8,637,684 B2
APPLICATION NO. : 13/101612
DATED : January 28, 2014
INVENTOR(S) : Ben Shen and Zhong-Yin Zhang It is certified that error appears in the above-identified patent and that said Letters Patent is hereby corrected as shown below:

In title page, item (56) References Cited - Other Publications, delete the 26th reference on page 1 "Takai, et aL, "Effects of modification of the hydrophobic C-1-C-16 segment of tautomycin on its affinity to type-1 and type-2A protein phosphatases," Biochem. J., 350:81-8, 2000." and replace with --Takai, et al., "Effects of modification of the hydrophobic C-1-C-16 segment of tautomycin on its affinity to type-1 and type-2A protein phosphatases," Biochem. J., 350:81-8, 2000.-- therefor.

In the Claims:

In claim 1, column 60, line 39, after --tautomycetin--, delete "thereof".

In claim 1, column 60, lines 41-52, delete the entire contents of lines 41-52 and insert

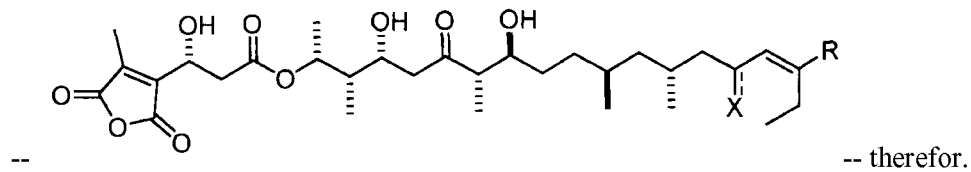

-- therefor.

In claim 2, column 60, line 55, delete "=OH" and insert -- –OH-- therefor.

In claim 13, column 61, line 58, after --immunotherapy,--, delete "chemotherapy".

In claim 17, column 62, line 56, after --tautomycetin--, delete "thereof".

In claim 20, column 64, line 4, after --tautomycetin--, delete "thereof".

Signed and Sealed this
Sixth Day of May, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,637,684 B2 | Page 1 of 1 |
| APPLICATION NO. | : 13/101612 | |
| DATED | : January 28, 2014 | |
| INVENTOR(S) | : Ben Shen et al. | |

It is certified that error appears in the above-identified patent and that said Letters Patent is hereby corrected as shown below:

In the Specification:

In column 1, lines 11-13, delete
"This invention was made with government support under CA113297 awarded by the National Institutes of Health. The government has certain rights in the invention."
and insert
--This invention was made with government support under CA113297, CA069202, and CA126937 awarded by the National Institutes of Health. The government has certain rights in the invention.--
therefor.

Signed and Sealed this
Seventeenth Day of June, 2014

Michelle K. Lee
*Deputy Director of the United States Patent and Trademark Office*